US012753436B2

(12) United States Patent
Milpied et al.

(10) Patent No.: US 12,753,436 B2
(45) Date of Patent: Oct. 6, 2026

(54) RNA SEQUENCING METHOD FOR THE ANALYSIS OF B AND T CELL TRANSCRIPTOME IN PHENOTYPICALLY DEFINED B AND T CELL SUBSETS

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ D'AIX MARSEILLE, Marseilles (FR)

(72) Inventors: Pierre Milpied, Marseilles (FR); Noudjoud Attaf, Marseilles (FR); Inaki Cervera-Marzal, Marseilles (FR); Laurine Gil, Marseilles (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITÉ D'AIX MARSEILLE, Marseilles (FR)

( * ) Notice: Subject to any disclaimer, the term of this patent is extended or adjusted under 35 U.S.C. 154(b) by 1193 days.

(21) Appl. No.: 17/633,750

(22) PCT Filed: Aug. 7, 2020

(86) PCT No.: PCT/EP2020/072223

§ 371 (c)(1),
(2) Date: Feb. 8, 2022

(87) PCT Pub. No.: WO2021/023853

PCT Pub. Date: Feb. 11, 2021

(65) Prior Publication Data

US 2022/0333194 A1 Oct. 20, 2022

(30) Foreign Application Priority Data

Aug. 8, 2019 (EP) .................................... 19190782

(51) Int. Cl.
*C12Q 1/6881* (2018.01)
*C12N 15/10* (2006.01)
*C12Q 1/6869* (2018.01)

(52) U.S. Cl.
CPC ....... *C12Q 1/6881* (2013.01); *C12N 15/1065* (2013.01); *C12N 15/1096* (2013.01);
(Continued)

(58) Field of Classification Search
None
See application file for complete search history.

(56) References Cited

U.S. PATENT DOCUMENTS

| | | | | |
|---|---|---|---|---|
| 8,877,916 B2 * | 11/2014 | Alexandrov | ......... | C07K 14/415 800/278 |
| 10,323,236 B2 * | 6/2019 | Liu | ...................... | C12Q 1/6874 |

(Continued)

FOREIGN PATENT DOCUMENTS

| | | | | |
|---|---|---|---|---|
| WO | WO-2014201273 A1 * | 12/2014 | ......... | C12N 15/1065 |
| WO | 2020136438 A1 | 7/2020 | | |

OTHER PUBLICATIONS

X-L Hou et al, "Current status and recent advances of next generation sequencing techniques in immunological repertoire", Genes and Immunity, vol. 17, No. 3, Apr. 1, 2016 (Apr. 1, 2016), p. 153-164.

*Primary Examiner* — Heather Calamita
*Assistant Examiner* — Elizabeth Rose Lafave
(74) *Attorney, Agent, or Firm* — WCF IP

(57) ABSTRACT

Single-cell RNA sequencing (scRNAseq) allows the identification, characterization, and quantification of cell types in a tissue. When focused on the adaptive immune system's T and B cells, scRNAseq carries the potential to track the clonal lineage of each analyzed cell through the unique rearranged sequence of its antigen receptor (TCR or BCR, respectively), and link it to the functional state inferred from transcriptome analysis. Computational approaches to infer clonality and maturation status (for BCR only) from scRNAseq datasets of T and B cells have been developed but (Continued)

Figure 1:
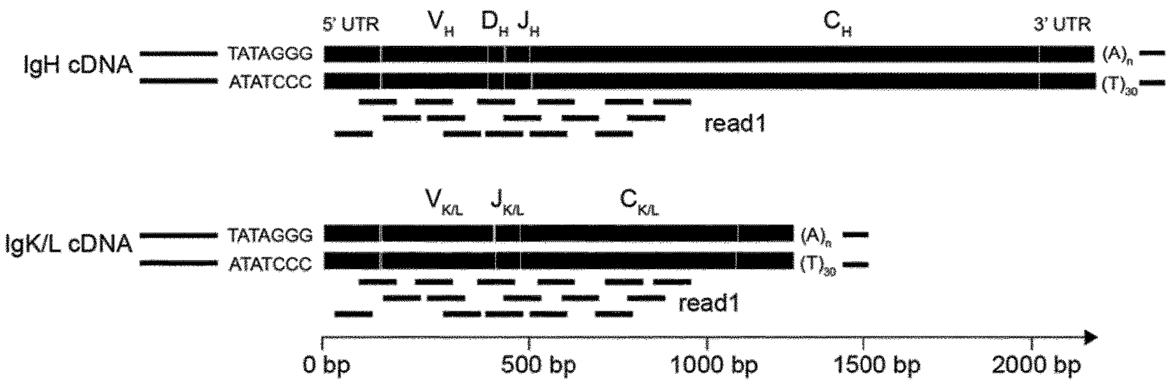

there are cumbersome and not costly effective. The inventors have now developed a FACS-based 5'-end RNAseq method, in particular a FACS-based 5'-end scRNAseq method, for cost effective integrative analysis of B and T cell transcriptome and paired BCR and TCR repertoire in phenotypically defined B and T cell subsets. In particular, the method of the present invention includes a reverse transcription step that uses a number of different well specific template switching oligonucleotides (TSO) to introduce a well-specific DNA barcode in the 5'-end of cDNAs.

14 Claims, 4 Drawing Sheets

Specification includes a Sequence Listing.

(52) U.S. Cl.
CPC ..... *C12Q 1/6869* (2013.01); *C12Q 2521/107* (2013.01); *C12Q 2525/121* (2013.01); *C12Q 2563/179* (2013.01)

(56) References Cited

U.S. PATENT DOCUMENTS

| | | | | |
|---|---|---|---|---|
| 2014/0066318 | A1* | 3/2014 | Frisen | G01N 1/30<br>506/3 |
| 2016/0244825 | A1 | 8/2016 | Vigneault | |
| 2016/0251714 | A1 | 9/2016 | Conant | |
| 2018/0282803 | A1 | 10/2018 | Belgrader | |

* cited by examiner

SEQUENCE LISTING

```
<160> NUMBER OF SEQ ID NOS: 251

<210> SEQ ID NO 1
<211> LENGTH: 21
<212> TYPE: DNA
<213> ORGANISM: Artificial
<220> FEATURE:
<223> OTHER INFORMATION: Synthetic PCR handle sequence

<400> SEQUENCE: 1

agacgtgtgc tcttccgatc t                                              21


<210> SEQ ID NO 2
<211> LENGTH: 8
<212> TYPE: DNA
<213> ORGANISM: Artificial
<220> FEATURE:
<223> OTHER INFORMATION: Synthetic barcode

<400> SEQUENCE: 2

cgtctaat                                                              8


<210> SEQ ID NO 3
<211> LENGTH: 8
<212> TYPE: DNA
<213> ORGANISM: Artificial
<220> FEATURE:
<223> OTHER INFORMATION: Synthetic barcode

<400> SEQUENCE: 3

agactcgt                                                              8


<210> SEQ ID NO 4
<211> LENGTH: 8
<212> TYPE: DNA
<213> ORGANISM: Artificial
<220> FEATURE:
<223> OTHER INFORMATION: Synthetic barcode

<400> SEQUENCE: 4

gcacgtca                                                              8


<210> SEQ ID NO 5
<211> LENGTH: 8
<212> TYPE: DNA
<213> ORGANISM: Artificial
<220> FEATURE:
<223> OTHER INFORMATION: Synthetic barcode
```

<400> SEQUENCE: 5 tcaacgac 8

<210> SEQ ID NO 6
<211> LENGTH: 8
<212> TYPE: DNA
<213> ORGANISM: Artificial
<220> FEATURE:
<223> OTHER INFORMATION: Synthetic barcode

<400> SEQUENCE: 6 atttagcg 8

<210> SEQ ID NO 7
<211> LENGTH: 8
<212> TYPE: DNA
<213> ORGANISM: Artificial
<220> FEATURE:
<223> OTHER INFORMATION: Synthetic barcode

<400> SEQUENCE: 7 atacagac 8

<210> SEQ ID NO 8
<211> LENGTH: 8
<212> TYPE: DNA
<213> ORGANISM: Artificial
<220> FEATURE:
<223> OTHER INFORMATION: Synthetic barcode

<400> SEQUENCE: 8 tgcgtagg 8

<210> SEQ ID NO 9
<211> LENGTH: 8
<212> TYPE: DNA
<213> ORGANISM: Artificial
<220> FEATURE:
<223> OTHER INFORMATION: Synthetic barcode

<400> SEQUENCE: 9 tggagctc 8

<210> SEQ ID NO 10
<211> LENGTH: 8
<212> TYPE: DNA
<213> ORGANISM: Artificial
<220> FEATURE:
<223> OTHER INFORMATION: Synthetic barcode

<400> SEQUENCE: 10 tgaatacc 8

<210> SEQ ID NO 11
<211> LENGTH: 8
<212> TYPE: DNA
<213> ORGANISM: Artificial
<220> FEATURE:
<223> OTHER INFORMATION: Synthetic barcode

<400> SEQUENCE: 11 tctcacac 8

<210> SEQ ID NO 12
<211> LENGTH: 8

<212> TYPE: DNA
<213> ORGANISM: Artificial
<220> FEATURE:
<223> OTHER INFORMATION: Synthetic barcode

<400> SEQUENCE: 12 tactggta 8

<210> SEQ ID NO 13
<211> LENGTH: 8
<212> TYPE: DNA
<213> ORGANISM: Artificial
<220> FEATURE:
<223> OTHER INFORMATION: Synthetic barcode

<400> SEQUENCE: 13 acgatagg 8

<210> SEQ ID NO 14
<211> LENGTH: 8
<212> TYPE: DNA
<213> ORGANISM: Artificial
<220> FEATURE:
<223> OTHER INFORMATION: Synthetic barcode

<400> SEQUENCE: 14 gatgtcga 8

<210> SEQ ID NO 15
<211> LENGTH: 8
<212> TYPE: DNA
<213> ORGANISM: Artificial
<220> FEATURE:
<223> OTHER INFORMATION: Synthetic barcode

<400> SEQUENCE: 15 ttacgggt 8

<210> SEQ ID NO 16
<211> LENGTH: 8
<212> TYPE: DNA
<213> ORGANISM: Artificial
<220> FEATURE:
<223> OTHER INFORMATION: Synthetic barcode

<400> SEQUENCE: 16 cacagcat 8

<210> SEQ ID NO 17
<211> LENGTH: 8
<212> TYPE: DNA
<213> ORGANISM: Artificial
<220> FEATURE:
<223> OTHER INFORMATION: Synthetic barcode

<400> SEQUENCE: 17 ctttgaca 8

<210> SEQ ID NO 18
<211> LENGTH: 8
<212> TYPE: DNA
<213> ORGANISM: Artificial
<220> FEATURE:
<223> OTHER INFORMATION: Synthetic barcode

<400> SEQUENCE: 18 cccttcaag 8

<210> SEQ ID NO 19
<211> LENGTH: 8
<212> TYPE: DNA
<213> ORGANISM: Artificial
<220> FEATURE:
<223> OTHER INFORMATION: Synthetic barcode

<400> SEQUENCE: 19 gagtcctg 8

<210> SEQ ID NO 20
<211> LENGTH: 8
<212> TYPE: DNA
<213> ORGANISM: Artificial
<220> FEATURE:
<223> OTHER INFORMATION: Synthetic barcode

<400> SEQUENCE: 20 cacactga 8

<210> SEQ ID NO 21
<211> LENGTH: 8
<212> TYPE: DNA
<213> ORGANISM: Artificial
<220> FEATURE:
<223> OTHER INFORMATION: Synthetic barcode

<400> SEQUENCE: 21 gttacagg 8

<210> SEQ ID NO 22
<211> LENGTH: 8
<212> TYPE: DNA
<213> ORGANISM: Artificial
<220> FEATURE:
<223> OTHER INFORMATION: Synthetic barcode

<400> SEQUENCE: 22 ggaccttt 8

<210> SEQ ID NO 23
<211> LENGTH: 8
<212> TYPE: DNA
<213> ORGANISM: Artificial
<220> FEATURE:
<223> OTHER INFORMATION: Synthetic barcode

<400> SEQUENCE: 23 ttccgttc 8

<210> SEQ ID NO 24
<211> LENGTH: 8
<212> TYPE: DNA
<213> ORGANISM: Artificial
<220> FEATURE:
<223> OTHER INFORMATION: Synthetic barcode

<400> SEQUENCE: 24 actgtttg 8

<210> SEQ ID NO 25
<211> LENGTH: 8
<212> TYPE: DNA
<213> ORGANISM: Artificial

<220> FEATURE:
<223> OTHER INFORMATION: Synthetic barcode

<400> SEQUENCE: 25 aagtggct 8

<210> SEQ ID NO 26
<211> LENGTH: 8
<212> TYPE: DNA
<213> ORGANISM: Artificial
<220> FEATURE:
<223> OTHER INFORMATION: Synthetic barcode

<400> SEQUENCE: 26 ctgtacaa 8

<210> SEQ ID NO 27
<211> LENGTH: 8
<212> TYPE: DNA
<213> ORGANISM: Artificial
<220> FEATURE:
<223> OTHER INFORMATION: Synthetic barcode

<400> SEQUENCE: 27 cgcaaagt 8

<210> SEQ ID NO 28
<211> LENGTH: 8
<212> TYPE: DNA
<213> ORGANISM: Artificial
<220> FEATURE:
<223> OTHER INFORMATION: Synthetic barcode

<400> SEQUENCE: 28 gtgcatga 8

<210> SEQ ID NO 29
<211> LENGTH: 8
<212> TYPE: DNA
<213> ORGANISM: Artificial
<220> FEATURE:
<223> OTHER INFORMATION: Synthetic barcode

<400> SEQUENCE: 29 gtcattag 8

<210> SEQ ID NO 30
<211> LENGTH: 8
<212> TYPE: DNA
<213> ORGANISM: Artificial
<220> FEATURE:
<223> OTHER INFORMATION: Synthetic barcode

<400> SEQUENCE: 30 agctcctt 8

<210> SEQ ID NO 31
<211> LENGTH: 8
<212> TYPE: DNA
<213> ORGANISM: Artificial
<220> FEATURE:
<223> OTHER INFORMATION: Synthetic barcode

<400> SEQUENCE: 31 tcacccga 8

<210> SEQ ID NO 32
<211> LENGTH: 8
<212> TYPE: DNA
<213> ORGANISM: Artificial
<220> FEATURE:
<223> OTHER INFORMATION: Synthetic barcode

<400> SEQUENCE: 32 gttgccac 8

<210> SEQ ID NO 33
<211> LENGTH: 8
<212> TYPE: DNA
<213> ORGANISM: Artificial
<220> FEATURE:
<223> OTHER INFORMATION: Synthetic barcode

<400> SEQUENCE: 33 tgtaccaa 8

<210> SEQ ID NO 34
<211> LENGTH: 8
<212> TYPE: DNA
<213> ORGANISM: Artificial
<220> FEATURE:
<223> OTHER INFORMATION: Synthetic barcode

<400> SEQUENCE: 34 aacgaggt 8

<210> SEQ ID NO 35
<211> LENGTH: 8
<212> TYPE: DNA
<213> ORGANISM: Artificial
<220> FEATURE:
<223> OTHER INFORMATION: Synthetic barcode

<400> SEQUENCE: 35 agccacca 8

<210> SEQ ID NO 36
<211> LENGTH: 8
<212> TYPE: DNA
<213> ORGANISM: Artificial
<220> FEATURE:
<223> OTHER INFORMATION: Synthetic barcode

<400> SEQUENCE: 36 ggtaatca 8

<210> SEQ ID NO 37
<211> LENGTH: 8
<212> TYPE: DNA
<213> ORGANISM: Artificial
<220> FEATURE:
<223> OTHER INFORMATION: Synthetic barcode

<400> SEQUENCE: 37 ccagtcca 8

<210> SEQ ID NO 38
<211> LENGTH: 8
<212> TYPE: DNA
<213> ORGANISM: Artificial
<220> FEATURE:
<223> OTHER INFORMATION: Synthetic barcode

<400> SEQUENCE: 38 acctcagc 8

<210> SEQ ID NO 39
<211> LENGTH: 8
<212> TYPE: DNA
<213> ORGANISM: Artificial
<220> FEATURE:
<223> OTHER INFORMATION: Synthetic barcode

<400> SEQUENCE: 39 ggtggact 8

<210> SEQ ID NO 40
<211> LENGTH: 8
<212> TYPE: DNA
<213> ORGANISM: Artificial
<220> FEATURE:
<223> OTHER INFORMATION: Synthetic barcode

<400> SEQUENCE: 40 gacaaacc 8

<210> SEQ ID NO 41
<211> LENGTH: 8
<212> TYPE: DNA
<213> ORGANISM: Artificial
<220> FEATURE:
<223> OTHER INFORMATION: Synthetic barcode

<400> SEQUENCE: 41 taactccg 8

<210> SEQ ID NO 42
<211> LENGTH: 8
<212> TYPE: DNA
<213> ORGANISM: Artificial
<220> FEATURE:
<223> OTHER INFORMATION: Synthetic barcode

<400> SEQUENCE: 42 acaccgtg 8

<210> SEQ ID NO 43
<211> LENGTH: 8
<212> TYPE: DNA
<213> ORGANISM: Artificial
<220> FEATURE:
<223> OTHER INFORMATION: Synthetic barcode

<400> SEQUENCE: 43 gtagaacg 8

<210> SEQ ID NO 44
<211> LENGTH: 8
<212> TYPE: DNA
<213> ORGANISM: Artificial
<220> FEATURE:
<223> OTHER INFORMATION: Synthetic barcode

<400> SEQUENCE: 44 ggattgac 8

<210> SEQ ID NO 45

<211> LENGTH: 8
<212> TYPE: DNA
<213> ORGANISM: Artificial
<220> FEATURE:
<223> OTHER INFORMATION: Synthetic barcode

<400> SEQUENCE: 45 acgtatcc 8

<210> SEQ ID NO 46
<211> LENGTH: 8
<212> TYPE: DNA
<213> ORGANISM: Artificial
<220> FEATURE:
<223> OTHER INFORMATION: Synthetic barcode

<400> SEQUENCE: 46 ttcggaaa 8

<210> SEQ ID NO 47
<211> LENGTH: 8
<212> TYPE: DNA
<213> ORGANISM: Artificial
<220> FEATURE:
<223> OTHER INFORMATION: Synthetic barcode

<400> SEQUENCE: 47 agttgtgt 8

<210> SEQ ID NO 48
<211> LENGTH: 8
<212> TYPE: DNA
<213> ORGANISM: Artificial
<220> FEATURE:
<223> OTHER INFORMATION: Synthetic barcode

<400> SEQUENCE: 48 aagcacat 8

<210> SEQ ID NO 49
<211> LENGTH: 8
<212> TYPE: DNA
<213> ORGANISM: Artificial
<220> FEATURE:
<223> OTHER INFORMATION: Synthetic barcode

<400> SEQUENCE: 49 ctgtcatt 8

<210> SEQ ID NO 50
<211> LENGTH: 8
<212> TYPE: DNA
<213> ORGANISM: Artificial
<220> FEATURE:
<223> OTHER INFORMATION: Synthetic barcode

<400> SEQUENCE: 50 gtcctata 8

<210> SEQ ID NO 51
<211> LENGTH: 8
<212> TYPE: DNA
<213> ORGANISM: Artificial
<220> FEATURE:
<223> OTHER INFORMATION: Synthetic barcode

<400> SEQUENCE: 51 ctacgctg 8

<210> SEQ ID NO 52
<211> LENGTH: 8
<212> TYPE: DNA
<213> ORGANISM: Artificial
<220> FEATURE:
<223> OTHER INFORMATION: Synthetic barcode

<400> SEQUENCE: 52 gggattgt 8

<210> SEQ ID NO 53
<211> LENGTH: 8
<212> TYPE: DNA
<213> ORGANISM: Artificial
<220> FEATURE:
<223> OTHER INFORMATION: Synthetic barcode

<400> SEQUENCE: 53 tgatgtag 8

<210> SEQ ID NO 54
<211> LENGTH: 8
<212> TYPE: DNA
<213> ORGANISM: Artificial
<220> FEATURE:
<223> OTHER INFORMATION: Synthetic barcode

<400> SEQUENCE: 54 ttcgctgt 8

<210> SEQ ID NO 55
<211> LENGTH: 8
<212> TYPE: DNA
<213> ORGANISM: Artificial
<220> FEATURE:
<223> OTHER INFORMATION: Synthetic barcode

<400> SEQUENCE: 55 gaagactt 8

<210> SEQ ID NO 56
<211> LENGTH: 8
<212> TYPE: DNA
<213> ORGANISM: Artificial
<220> FEATURE:
<223> OTHER INFORMATION: Synthetic barcode

<400> SEQUENCE: 56 tctgggca 8

<210> SEQ ID NO 57
<211> LENGTH: 8
<212> TYPE: DNA
<213> ORGANISM: Artificial
<220> FEATURE:
<223> OTHER INFORMATION: Synthetic barcode

<400> SEQUENCE: 57 caactaga 8

<210> SEQ ID NO 58
<211> LENGTH: 8
<212> TYPE: DNA

<213> ORGANISM: Artificial
<220> FEATURE:
<223> OTHER INFORMATION: Synthetic barcode

<400> SEQUENCE: 58 ccatggga 8

<210> SEQ ID NO 59
<211> LENGTH: 8
<212> TYPE: DNA
<213> ORGANISM: Artificial
<220> FEATURE:
<223> OTHER INFORMATION: Synthetic barcode

<400> SEQUENCE: 59 atgcgacg 8

<210> SEQ ID NO 60
<211> LENGTH: 8
<212> TYPE: DNA
<213> ORGANISM: Artificial
<220> FEATURE:
<223> OTHER INFORMATION: Synthetic barcode

<400> SEQUENCE: 60 gagggtag 8

<210> SEQ ID NO 61
<211> LENGTH: 8
<212> TYPE: DNA
<213> ORGANISM: Artificial
<220> FEATURE:
<223> OTHER INFORMATION: Synthetic barcode

<400> SEQUENCE: 61 cgggtgaa 8

<210> SEQ ID NO 62
<211> LENGTH: 8
<212> TYPE: DNA
<213> ORGANISM: Artificial
<220> FEATURE:
<223> OTHER INFORMATION: Synthetic barcode

<400> SEQUENCE: 62 gccatctt 8

<210> SEQ ID NO 63
<211> LENGTH: 8
<212> TYPE: DNA
<213> ORGANISM: Artificial
<220> FEATURE:
<223> OTHER INFORMATION: Synthetic barcode

<400> SEQUENCE: 63 gcataatc 8

<210> SEQ ID NO 64
<211> LENGTH: 8
<212> TYPE: DNA
<213> ORGANISM: Artificial
<220> FEATURE:
<223> OTHER INFORMATION: Synthetic barcode

<400> SEQUENCE: 64 tctatggt 8

<210> SEQ ID NO 65
<211> LENGTH: 8
<212> TYPE: DNA
<213> ORGANISM: Artificial
<220> FEATURE:
<223> OTHER INFORMATION: Synthetic barcode

<400> SEQUENCE: 65 aggactta 8

<210> SEQ ID NO 66
<211> LENGTH: 8
<212> TYPE: DNA
<213> ORGANISM: Artificial
<220> FEATURE:
<223> OTHER INFORMATION: Synthetic barcode

<400> SEQUENCE: 66 cgtgattc 8

<210> SEQ ID NO 67
<211> LENGTH: 8
<212> TYPE: DNA
<213> ORGANISM: Artificial
<220> FEATURE:
<223> OTHER INFORMATION: Synthetic barcode

<400> SEQUENCE: 67 actagcga 8

<210> SEQ ID NO 68
<211> LENGTH: 8
<212> TYPE: DNA
<213> ORGANISM: Artificial
<220> FEATURE:
<223> OTHER INFORMATION: Synthetic barcode

<400> SEQUENCE: 68 gtaactcc 8

<210> SEQ ID NO 69
<211> LENGTH: 8
<212> TYPE: DNA
<213> ORGANISM: Artificial
<220> FEATURE:
<223> OTHER INFORMATION: Synthetic barcode

<400> SEQUENCE: 69 cggaagtg 8

<210> SEQ ID NO 70
<211> LENGTH: 8
<212> TYPE: DNA
<213> ORGANISM: Artificial
<220> FEATURE:
<223> OTHER INFORMATION: Synthetic barcode

<400> SEQUENCE: 70 ccgagtac 8

<210> SEQ ID NO 71
<211> LENGTH: 8
<212> TYPE: DNA
<213> ORGANISM: Artificial
<220> FEATURE:

<223> OTHER INFORMATION: Synthetic barcode

<400> SEQUENCE: 71 gacgcaat 8

<210> SEQ ID NO 72
<211> LENGTH: 8
<212> TYPE: DNA
<213> ORGANISM: Artificial
<220> FEATURE:
<223> OTHER INFORMATION: Synthetic barcode

<400> SEQUENCE: 72 acctggag 8

<210> SEQ ID NO 73
<211> LENGTH: 8
<212> TYPE: DNA
<213> ORGANISM: Artificial
<220> FEATURE:
<223> OTHER INFORMATION: Synthetic barcode

<400> SEQUENCE: 73 catgggtt 8

<210> SEQ ID NO 74
<211> LENGTH: 8
<212> TYPE: DNA
<213> ORGANISM: Artificial
<220> FEATURE:
<223> OTHER INFORMATION: Synthetic barcode

<400> SEQUENCE: 74 attcctag 8

<210> SEQ ID NO 75
<211> LENGTH: 8
<212> TYPE: DNA
<213> ORGANISM: Artificial
<220> FEATURE:
<223> OTHER INFORMATION: Synthetic barcode

<400> SEQUENCE: 75 aatcatgc 8

<210> SEQ ID NO 76
<211> LENGTH: 8
<212> TYPE: DNA
<213> ORGANISM: Artificial
<220> FEATURE:
<223> OTHER INFORMATION: Synthetic barcode

<400> SEQUENCE: 76 gcttccct 8

<210> SEQ ID NO 77
<211> LENGTH: 8
<212> TYPE: DNA
<213> ORGANISM: Artificial
<220> FEATURE:
<223> OTHER INFORMATION: Synthetic barcode

<400> SEQUENCE: 77 aggtaaag 8

<210> SEQ ID NO 78
<211> LENGTH: 8
<212> TYPE: DNA
<213> ORGANISM: Artificial
<220> FEATURE:
<223> OTHER INFORMATION: Synthetic barcode

<400> SEQUENCE: 78 ccacaact 8

<210> SEQ ID NO 79
<211> LENGTH: 8
<212> TYPE: DNA
<213> ORGANISM: Artificial
<220> FEATURE:
<223> OTHER INFORMATION: Synthetic barcode

<400> SEQUENCE: 79 acaggcat 8

<210> SEQ ID NO 80
<211> LENGTH: 8
<212> TYPE: DNA
<213> ORGANISM: Artificial
<220> FEATURE:
<223> OTHER INFORMATION: Synthetic barcode

<400> SEQUENCE: 80 tttgtgtc 8

<210> SEQ ID NO 81
<211> LENGTH: 8
<212> TYPE: DNA
<213> ORGANISM: Artificial
<220> FEATURE:
<223> OTHER INFORMATION: Synthetic barcode

<400> SEQUENCE: 81 tgagcata 8

<210> SEQ ID NO 82
<211> LENGTH: 8
<212> TYPE: DNA
<213> ORGANISM: Artificial
<220> FEATURE:
<223> OTHER INFORMATION: Synthetic barcode

<400> SEQUENCE: 82 ttagacgc 8

<210> SEQ ID NO 83
<211> LENGTH: 8
<212> TYPE: DNA
<213> ORGANISM: Artificial
<220> FEATURE:
<223> OTHER INFORMATION: Synthetic barcode

<400> SEQUENCE: 83 cgcttgct 8

<210> SEQ ID NO 84
<211> LENGTH: 8
<212> TYPE: DNA
<213> ORGANISM: Artificial
<220> FEATURE:
<223> OTHER INFORMATION: Synthetic barcode

<400> SEQUENCE: 84 agtctgcc 8

<210> SEQ ID NO 85
<211> LENGTH: 8
<212> TYPE: DNA
<213> ORGANISM: Artificial
<220> FEATURE:
<223> OTHER INFORMATION: Synthetic barcode

<400> SEQUENCE: 85 catagtcg 8

<210> SEQ ID NO 86
<211> LENGTH: 8
<212> TYPE: DNA
<213> ORGANISM: Artificial
<220> FEATURE:
<223> OTHER INFORMATION: Synthetic barcode

<400> SEQUENCE: 86 tcttgctg 8

<210> SEQ ID NO 87
<211> LENGTH: 8
<212> TYPE: DNA
<213> ORGANISM: Artificial
<220> FEATURE:
<223> OTHER INFORMATION: Synthetic barcode

<400> SEQUENCE: 87 gggacaac 8

<210> SEQ ID NO 88
<211> LENGTH: 8
<212> TYPE: DNA
<213> ORGANISM: Artificial
<220> FEATURE:
<223> OTHER INFORMATION: Synthetic barcode

<400> SEQUENCE: 88 atattccc 8

<210> SEQ ID NO 89
<211> LENGTH: 8
<212> TYPE: DNA
<213> ORGANISM: Artificial
<220> FEATURE:
<223> OTHER INFORMATION: Synthetic barcode

<400> SEQUENCE: 89 tgttaagc 8

<210> SEQ ID NO 90
<211> LENGTH: 8
<212> TYPE: DNA
<213> ORGANISM: Artificial
<220> FEATURE:
<223> OTHER INFORMATION: Synthetic barcode

<400> SEQUENCE: 90 tacgcctc 8

<210> SEQ ID NO 91
<211> LENGTH: 8

<212> TYPE: DNA
<213> ORGANISM: Artificial
<220> FEATURE:
<223> OTHER INFORMATION: Synthetic barcode

<400> SEQUENCE: 91 cacttatc 8

<210> SEQ ID NO 92
<211> LENGTH: 8
<212> TYPE: DNA
<213> ORGANISM: Artificial
<220> FEATURE:
<223> OTHER INFORMATION: Synthetic barcode

<400> SEQUENCE: 92 accgctaa 8

<210> SEQ ID NO 93
<211> LENGTH: 8
<212> TYPE: DNA
<213> ORGANISM: Artificial
<220> FEATURE:
<223> OTHER INFORMATION: Synthetic barcode

<400> SEQUENCE: 93 taaggtcc 8

<210> SEQ ID NO 94
<211> LENGTH: 8
<212> TYPE: DNA
<213> ORGANISM: Artificial
<220> FEATURE:
<223> OTHER INFORMATION: Synthetic barcode

<400> SEQUENCE: 94 gaaaggtg 8

<210> SEQ ID NO 95
<211> LENGTH: 8
<212> TYPE: DNA
<213> ORGANISM: Artificial
<220> FEATURE:
<223> OTHER INFORMATION: Synthetic barcode

<400> SEQUENCE: 95 acgttgta 8

<210> SEQ ID NO 96
<211> LENGTH: 8
<212> TYPE: DNA
<213> ORGANISM: Artificial
<220> FEATURE:
<223> OTHER INFORMATION: Synthetic barcode

<400> SEQUENCE: 96 gcagagaa 8

<210> SEQ ID NO 97
<211> LENGTH: 8
<212> TYPE: DNA
<213> ORGANISM: Artificial
<220> FEATURE:
<223> OTHER INFORMATION: Synthetic barcode

<400> SEQUENCE: 97 gcatttgg 8

<210> SEQ ID NO 98
<211> LENGTH: 4
<212> TYPE: DNA
<213> ORGANISM: Artificial
<220> FEATURE:
<223> OTHER INFORMATION: Synthetic insulator

<400> SEQUENCE: 98 tata 4

<210> SEQ ID NO 99
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 99
agacgtgtgc tcttccgatc tcgtctaatn nnnntatagg g 41

<210> SEQ ID NO 100
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 100
agacgtgtgc tcttccgatc tagactcgtn nnnntatagg g 41

<210> SEQ ID NO 101
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, or t

<400> SEQUENCE: 101
agacgtgtgc tcttccgatc tgcacgtcan nnnntatagg g 41

<210> SEQ ID NO 102
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 102
agacgtgtgc tcttccgatc ttcaacgacn nnnntatagg g 41

<210> SEQ ID NO 103
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 103
agacgtgtgc tcttccgatc tatttagcgn nnnntatagg g 41

<210> SEQ ID NO 104
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 104
agacgtgtgc tcttccgatc tatacagacn nnnntatagg g 41

<210> SEQ ID NO 105
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 105
agacgtgtgc tcttccgatc ttgcgtaggn nnnntatagg g 41

<210> SEQ ID NO 106
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 106
agacgtgtgc tcttccgatc ttggagctcn nnnntatagg g 41

<210> SEQ ID NO 107
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 107
agacgtgtgc tcttccgatc ttgaataccn nnnntatagg g 41

<210> SEQ ID NO 108
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 108
agacgtgtgc tcttccgatc ttctcacacn nnnntatagg g 41

<210> SEQ ID NO 109
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 109
agacgtgtgc tcttccgatc ttactggtan nnnntatagg g 41

<210> SEQ ID NO 110
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 110
agacgtgtgc tcttccgatc tacgataggn nnnntatagg g 41

<210> SEQ ID NO 111
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 111
agacgtgtgc tcttccgatc tgatgtcgan nnnntatagg g 41

<210> SEQ ID NO 112
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, or t

<400> SEQUENCE: 112
agacgtgtgc tcttccgatc tttacgggtn nnnntatagg g 41

<210> SEQ ID NO 113
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, or t

<400> SEQUENCE: 113
agacgtgtgc tcttccgatc tgaatgagtn nnnntatagg g 41

<210> SEQ ID NO 114
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 114
agacgtgtgc tcttccgatc tctttgacan nnnntatagg g 41

<210> SEQ ID NO 115
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 115
agacgtgtgc tcttccgatc tagagatctn nnnntatagg g 41

<210> SEQ ID NO 116
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 116
agacgtgtgc tcttccgatc tgagtcctgn nnnntatagg g 41

<210> SEQ ID NO 117
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 117
agacgtgtgc tcttccgatc tcacactgan nnnntatagg g 41

<210> SEQ ID NO 118
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 118
agacgtgtgc tcttccgatc tgttacaggn nnnntatagg g 41

<210> SEQ ID NO 119
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 119
agacgtgtgc tcttccgatc tggacctttn nnnntatagg g 41

<210> SEQ ID NO 120
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 120
agacgtgtgc tcttccgatc ttagactatn nnnntatagg g 41

<210> SEQ ID NO 121
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 121
agacgtgtgc tcttccgatc tactgtttgn nnnntatagg g 41

<210> SEQ ID NO 122
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 122
agacgtgtgc tcttccgatc taagtggctn nnnntatagg g 41

<210> SEQ ID NO 123
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, or t

<400> SEQUENCE: 123
agacgtgtgc tcttccgatc ttgctctcan nnnntatagg g 41

<210> SEQ ID NO 124
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 124
agacgtgtgc tcttccgatc tcggcgtggn nnnntatagg g 41

<210> SEQ ID NO 125
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 125
agacgtgtgc tcttccgatc tgtgcatgan nnnntatagg g 41

<210> SEQ ID NO 126
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 126
agacgtgtgc tcttccgatc tgtcattagn nnnntatagg g 41

<210> SEQ ID NO 127
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 127
agacgtgtgc tcttccgatc tagctccttn nnnntatagg g 41

<210> SEQ ID NO 128
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 128
agacgtgtgc tcttccgatc ttcacccgan nnnntatagg g 41

<210> SEQ ID NO 129
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 129
agacgtgtgc tcttccgatc tgttgccacn nnnntatagg g 41

<210> SEQ ID NO 130
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 130
agacgtgtgc tcttccgatc tctaatgcgn nnnntatagg g 41

<210> SEQ ID NO 131
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 131
agacgtgtgc tcttccgatc taacgaggtn nnnntatagg g 41

<210> SEQ ID NO 132
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 132
agacgtgtgc tcttccgatc tagccaccan nnnntatagg g 41

<210> SEQ ID NO 133
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 133
agacgtgtgc tcttccgatc ttagtgaacn nnnntatagg g 41

<210> SEQ ID NO 134
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 134
agacgtgtgc tcttccgatc tccagtccan nnnntatagg g 41

<210> SEQ ID NO 135
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 135
agacgtgtgc tcttccgatc tacctcagcn nnnntatagg g 41

<210> SEQ ID NO 136
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 136
agacgtgtgc tcttccgatc tggtggactn nnnntatagg g 41

<210> SEQ ID NO 137
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)

<223> OTHER INFORMATION: n is a, c, g, t or u

<400> SEQUENCE: 137
agacgtgtgc tcttccgatc tccggcgtcn nnnntatagg g 41

<210> SEQ ID NO 138
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 138
agacgtgtgc tcttccgatc ttaactccgn nnnntatagg g 41

<210> SEQ ID NO 139
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 139
agacgtgtgc tcttccgatc tacaccgtgn nnnntatagg g 41

<210> SEQ ID NO 140
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 140
agacgtgtgc tcttccgatc tgtagaacgn nnnntatagg g 41

<210> SEQ ID NO 141
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 141
agacgtgtgc tcttccgatc tggattgacn nnnntatagg g 41

<210> SEQ ID NO 142
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 142
agacgtgtgc tcttccgatc tacgtatccn nnnntatagg g 41

<210> SEQ ID NO 143
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 143
agacgtgtgc tcttccgatc tttcggaaan nnnntatagg g 41

<210> SEQ ID NO 144
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 144
agacgtgtgc tcttccgatc tagttgtgtn nnnntatagg g 41

<210> SEQ ID NO 145
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 145
agacgtgtgc tcttccgatc taagcacatn nnnntatagg g 41

<210> SEQ ID NO 146
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 146
agacgtgtgc tcttccgatc tctgtcattn nnnntatagg g 41

<210> SEQ ID NO 147
<211> LENGTH: 41
<212> TYPE: DNA
<213> ORGANISM: Artificial
<220> FEATURE:
<223> OTHER INFORMATION: Synthetic TSO
<220> FEATURE:

<221> NAME/KEY: misc_feature
<222> LOCATION: (30)..(34)
<223> OTHER INFORMATION: n is a, c, g, t or u

<400> SEQUENCE: 147
agacgtgtgc tcttccgatc taacattctn nnnntatagg g 41

<210> SEQ ID NO 148
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 148
agacgtgtgc tcttccgatc tctacgctgn nnnntatagg g 41

<210> SEQ ID NO 149
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 149
agacgtgtgc tcttccgatc tgggattgtn nnnntatagg g 41

<210> SEQ ID NO 150
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 150
agacgtgtgc tcttccgatc ttgatgtagn nnnntatagg g 41

<210> SEQ ID NO 151
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 151
agacgtgtgc tcttccgatc tttcgctgtn nnnntatagg g 41

<210> SEQ ID NO 152
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 152
agacgtgtgc tcttccgatc tgaagacttn nnnntatagg g 41

<210> SEQ ID NO 153
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 153
agacgtgtgc tcttccgatc ttctgggcan nnnntatagg g 41

<210> SEQ ID NO 154
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 154
agacgtgtgc tcttccgatc ttcgctacan nnnntatagg g 41

<210> SEQ ID NO 155
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 155
agacgtgtgc tcttccgatc tgtgttagcn nnnntatagg g 41

<210> SEQ ID NO 156
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 156
agacgtgtgc tcttccgatc tatgcgacgn nnnntatagg g 41

<210> SEQ ID NO 157
<211> LENGTH: 41
<212> TYPE: DNA
<213> ORGANISM: Artificial
<220> FEATURE:

<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 157
agacgtgtgc tcttccgatc tgagggtagn nnnntatagg g 41

<210> SEQ ID NO 158
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 158
agacgtgtgc tcttccgatc tcgggtgaan nnnntatagg g 41

<210> SEQ ID NO 159
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 159
agacgtgtgc tcttccgatc tgccatcttn nnnntatagg g 41

<210> SEQ ID NO 160
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 160
agacgtgtgc tcttccgatc ttgcgacatn nnnntatagg g 41

<210> SEQ ID NO 161
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 161
agacgtgtgc tcttccgatc ttctatggtn nnnntatagg g 41

<210> SEQ ID NO 162
<211> LENGTH: 41
<212> TYPE: DNA
<213> ORGANISM: Artificial

<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 162
agacgtgtgc tcttccgatc taggacttan nnnntatagg g 41

<210> SEQ ID NO 163
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 163
agacgtgtgc tcttccgatc tccgctcagn nnnntatagg g 41

<210> SEQ ID NO 164
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 164
agacgtgtgc tcttccgatc tactagcgan nnnntatagg g 41

<210> SEQ ID NO 165
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 165
agacgtgtgc tcttccgatc tgtaactccn nnnntatagg g 41

<210> SEQ ID NO 166
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 166
agacgtgtgc tcttccgatc tcggaagtgn nnnntatagg g 41

<210> SEQ ID NO 167
<211> LENGTH: 41
<212> TYPE: DNA

<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 167
agacgtgtgc tcttccgatc tccgagtacn nnnntatagg g 41

<210> SEQ ID NO 168
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 168
agacgtgtgc tcttccgatc tgatctgagn nnnntatagg g 41

<210> SEQ ID NO 169
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 169
agacgtgtgc tcttccgatc tacctggagn nnnntatagg g 41

<210> SEQ ID NO 170
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 170
agacgtgtgc tcttccgatc tcatgggttn nnnntatagg g 41

<210> SEQ ID NO 171
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 171
agacgtgtgc tcttccgatc tattcctagn nnnntatagg g 41

<210> SEQ ID NO 172
<211> LENGTH: 41

<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 172
agacgtgtgc tcttccgatc ttcgaaccgn nnnntatagg g 41

<210> SEQ ID NO 173
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 173
agacgtgtgc tcttccgatc ttccacactn nnnntatagg g 41

<210> SEQ ID NO 174
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 174
agacgtgtgc tcttccgatc taggtaaagn nnnntatagg g 41

<210> SEQ ID NO 175
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 175
agacgtgtgc tcttccgatc ttaggcgcgn nnnntatagg g 41

<210> SEQ ID NO 176
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 176
agacgtgtgc tcttccgatc tacaggcatn nnnntatagg g 41

<210> SEQ ID NO 177

<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 177
agacgtgtgc tcttccgatc ttttgtgtcn nnnntatagg g 41

<210> SEQ ID NO 178
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 178
agacgtgtgc tcttccgatc ttgagcatan nnnntatagg g 41

<210> SEQ ID NO 179
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 179
agacgtgtgc tcttccgatc tttagacgcn nnnntatagg g 41

<210> SEQ ID NO 180
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 180
agacgtgtgc tcttccgatc tcgcttgctn nnnntatagg g 41

<210> SEQ ID NO 181
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 181
agacgtgtgc tcttccgatc tattggagcn nnnntatagg g 41

<210> SEQ ID NO 182
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 182
agacgtgtgc tcttccgatc tcatagtcgn nnnntatagg g 41

<210> SEQ ID NO 183
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 183
agacgtgtgc tcttccgatc ttcttgctgn nnnntatagg g 41

<210> SEQ ID NO 184
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 184
agacgtgtgc tcttccgatc tgggacaacn nnnntatagg g 41

<210> SEQ ID NO 185
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 185
agacgtgtgc tcttccgatc tatattcccn nnnntatagg g 41

<210> SEQ ID NO 186
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 186
agacgtgtgc tcttccgatc ttgttaagcn nnnntatagg g 41

<210> SEQ ID NO 187
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 187
agacgtgtgc tcttccgatc ttacgcctcn nnnntatagg g 41

<210> SEQ ID NO 188
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 188
agacgtgtgc tcttccgatc tcacttatcn nnnntatagg g 41

<210> SEQ ID NO 189
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 189
agacgtgtgc tcttccgatc taccgctaan nnnntatagg g 41

<210> SEQ ID NO 190
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 190
agacgtgtgc tcttccgatc ttaaggtccn nnnntatagg g 41

<210> SEQ ID NO 191
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 191
agacgtgtgc tcttccgatc tgaaaggtgn nnnntatagg g 41

<210> SEQ ID NO 192
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 192
agacgtgtgc tcttccgatc tacgttgtan nnnntatagg g 41

<210> SEQ ID NO 193
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 193
agacgtgtgc tcttccgatc tgtctgccgn nnnntatagg g 41

<210> SEQ ID NO 194
<211> LENGTH: 41
<212> TYPE: DNA
<213> ORGANISM: Artificial
<220> FEATURE:
<223> OTHER INFORMATION: Synthetic TSO
<220> FEATURE:
<221> NAME/KEY: misc_feature
<222> LOCATION: (30)..(34)
<223> OTHER INFORMATION: n is a, c, g, t or u

<400> SEQUENCE: 194
agacgtgtgc tcttccgatc tgcatttggn nnnntatagg g 41

<210> SEQ ID NO 195
<211> LENGTH: 53
<212> TYPE: DNA
<213> ORGANISM: Artificial
<220> FEATURE:
<223> OTHER INFORMATION: Synthetic oligo dT RT primer
<220> FEATURE:
<221> NAME/KEY: misc_feature
<222> LOCATION: (52)..(52)
<223> OTHER INFORMATION: N represents dG, dA, or dC
<220> FEATURE:
<221> NAME/KEY: misc_feature
<222> LOCATION: (53)..(53)
<223> OTHER INFORMATION: N represents dA, dT, dG, or dC

<400> SEQUENCE: 195
tgcggtatct aaagcggtga gttttttttt tttttttttt tttttttttt tnn 53

<210> SEQ ID NO 196
<211> LENGTH: 21
<212> TYPE: DNA
<213> ORGANISM: Artificial
<220> FEATURE:
<223> OTHER INFORMATION: Synthetic primer

<400> SEQUENCE: 196
agacgtgtgc tcttccgatc t 21

<210> SEQ ID NO 197
<211> LENGTH: 21
<212> TYPE: DNA
<213> ORGANISM: Artificial
<220> FEATURE:
<223> OTHER INFORMATION: Synthetic primer

<400> SEQUENCE: 197
tgcggtatct aaagcggtga g 21

<210> SEQ ID NO 198
<211> LENGTH: 8
<212> TYPE: DNA
<213> ORGANISM: Artificial
<220> FEATURE:
<223> OTHER INFORMATION: Synthetic barcode

<400> SEQUENCE: 198 ctaccagg 8

<210> SEQ ID NO 199
<211> LENGTH: 8
<212> TYPE: DNA
<213> ORGANISM: Artificial
<220> FEATURE:
<223> OTHER INFORMATION: Synthetic barcode

<400> SEQUENCE: 199 catgctta 8

<210> SEQ ID NO 200
<211> LENGTH: 8
<212> TYPE: DNA
<213> ORGANISM: Artificial
<220> FEATURE:
<223> OTHER INFORMATION: Synthetic barcode

<400> SEQUENCE: 200 gcacatct 8

<210> SEQ ID NO 201
<211> LENGTH: 8
<212> TYPE: DNA
<213> ORGANISM: Artificial
<220> FEATURE:
<223> OTHER INFORMATION: Synthetic barcode

<400> SEQUENCE: 201 tgctcgac 8

<210> SEQ ID NO 202
<211> LENGTH: 8
<212> TYPE: DNA
<213> ORGANISM: Artificial
<220> FEATURE:
<223> OTHER INFORMATION: Synthetic barcode

<400> SEQUENCE: 202 agcaattc 8

<210> SEQ ID NO 203
<211> LENGTH: 8
<212> TYPE: DNA
<213> ORGANISM: Artificial

<220> FEATURE:
<223> OTHER INFORMATION: Synthetic barcode

<400> SEQUENCE: 203 agttgctt 8

<210> SEQ ID NO 204
<211> LENGTH: 8
<212> TYPE: DNA
<213> ORGANISM: Artificial
<220> FEATURE:
<223> OTHER INFORMATION: Synthetic barcode

<400> SEQUENCE: 204 ccagttag 8

<210> SEQ ID NO 205
<211> LENGTH: 8
<212> TYPE: DNA
<213> ORGANISM: Artificial
<220> FEATURE:
<223> OTHER INFORMATION: Synthetic barcode

<400> SEQUENCE: 205 ttgagcct 8

<210> SEQ ID NO 206
<211> LENGTH: 8
<212> TYPE: DNA
<213> ORGANISM: Artificial
<220> FEATURE:
<223> OTHER INFORMATION: Synthetic barcode

<400> SEQUENCE: 206 accaactg 8

<210> SEQ ID NO 207
<211> LENGTH: 8
<212> TYPE: DNA
<213> ORGANISM: Artificial
<220> FEATURE:
<223> OTHER INFORMATION: Synthetic barcode

<400> SEQUENCE: 207 ggtccaga 8

<210> SEQ ID NO 208
<211> LENGTH: 8
<212> TYPE: DNA
<213> ORGANISM: Artificial
<220> FEATURE:
<223> OTHER INFORMATION: Synthetic barcode

<400> SEQUENCE: 208 gtataaca 8

<210> SEQ ID NO 209
<211> LENGTH: 8
<212> TYPE: DNA
<213> ORGANISM: Artificial
<220> FEATURE:
<223> OTHER INFORMATION: Synthetic barcode

<400> SEQUENCE: 209 ttcgctga 8

<210> SEQ ID NO 210
<211> LENGTH: 8
<212> TYPE: DNA
<213> ORGANISM: Artificial
<220> FEATURE:
<223> OTHER INFORMATION: Synthetic barcode

<400> SEQUENCE: 210 aacttgac 8

<210> SEQ ID NO 211
<211> LENGTH: 8
<212> TYPE: DNA
<213> ORGANISM: Artificial
<220> FEATURE:
<223> OTHER INFORMATION: Synthetic barcode

<400> SEQUENCE: 211 cacatcct 8

<210> SEQ ID NO 212
<211> LENGTH: 8
<212> TYPE: DNA
<213> ORGANISM: Artificial
<220> FEATURE:
<223> OTHER INFORMATION: Synthetic barcode

<400> SEQUENCE: 212 tcggaatg 8

<210> SEQ ID NO 213
<211> LENGTH: 8
<212> TYPE: DNA
<213> ORGANISM: Artificial
<220> FEATURE:
<223> OTHER INFORMATION: Synthetic barcode

<400> SEQUENCE: 213 aaggatgt 8

<210> SEQ ID NO 214
<211> LENGTH: 66
<212> TYPE: DNA
<213> ORGANISM: Artificial
<220> FEATURE:
<223> OTHER INFORMATION: Synthetic adapter

<400> SEQUENCE: 214
caagcagaag acggcatacg agatcctggt aggtgactgg agttcagacg tgtgctcttc 60
cgatct 66

<210> SEQ ID NO 215
<211> LENGTH: 66
<212> TYPE: DNA
<213> ORGANISM: Artificial
<220> FEATURE:
<223> OTHER INFORMATION: Synthetic adapter

<400> SEQUENCE: 215
caagcagaag acggcatacg agattaagca tggtgactgg agttcagacg tgtgctcttc 60
cgatct 66

<210> SEQ ID NO 216
<211> LENGTH: 66

<212> TYPE: DNA
<213> ORGANISM: Artificial
<220> FEATURE:
<223> OTHER INFORMATION: Synthetic adapter

<400> SEQUENCE: 216
caagcagaag acggcatacg agatagatgt gcgtgactgg agttcagacg tgtgctcttc 60
cgatct 66

<210> SEQ ID NO 217
<211> LENGTH: 66
<212> TYPE: DNA
<213> ORGANISM: Artificial
<220> FEATURE:
<223> OTHER INFORMATION: Synthetic adapter

<400> SEQUENCE: 217
caagcagaag acggcatacg agatgtcgag cagtgactgg agttcagacg tgtgctcttc 60
cgatct 66

<210> SEQ ID NO 218
<211> LENGTH: 66
<212> TYPE: DNA
<213> ORGANISM: Artificial
<220> FEATURE:
<223> OTHER INFORMATION: Synthetic adapter

<400> SEQUENCE: 218
caagcagaag acggcatacg agatgaattg ctgtgactgg agttcagacg tgtgctcttc 60
cgatct 66

<210> SEQ ID NO 219
<211> LENGTH: 66
<212> TYPE: DNA
<213> ORGANISM: Artificial
<220> FEATURE:
<223> OTHER INFORMATION: Synthetic adapter

<400> SEQUENCE: 219
caagcagaag acggcatacg agataagcaa ctgtgactgg agttcagacg tgtgctcttc 60
cgatct 66

<210> SEQ ID NO 220
<211> LENGTH: 66
<212> TYPE: DNA
<213> ORGANISM: Artificial
<220> FEATURE:
<223> OTHER INFORMATION: Synthetic adapter

<400> SEQUENCE: 220
caagcagaag acggcatacg agatctaact gggtgactgg agttcagacg tgtgctcttc 60
cgatct 66

<210> SEQ ID NO 221
<211> LENGTH: 66
<212> TYPE: DNA
<213> ORGANISM: Artificial
<220> FEATURE:
<223> OTHER INFORMATION: Synthetic adapter

<400> SEQUENCE: 221
caagcagaag acggcatacg agataggctc aagtgactgg agttcagacg tgtgctcttc 60
cgatct 66

<210> SEQ ID NO 222
<211> LENGTH: 66
<212> TYPE: DNA
<213> ORGANISM: Artificial
<220> FEATURE:
<223> OTHER INFORMATION: Synthetic adapter

<400> SEQUENCE: 222
caagcagaag acggcatacg agatcagttg gtgtgactgg agttcagacg tgtgctcttc 60
cgatct 66

<210> SEQ ID NO 223
<211> LENGTH: 66
<212> TYPE: DNA
<213> ORGANISM: Artificial
<220> FEATURE:
<223> OTHER INFORMATION: Synthetic adapter

<400> SEQUENCE: 223
caagcagaag acggcatacg agattctgga ccgtgactgg agttcagacg tgtgctcttc 60
cgatct 66

<210> SEQ ID NO 224
<211> LENGTH: 66
<212> TYPE: DNA
<213> ORGANISM: Artificial
<220> FEATURE:
<223> OTHER INFORMATION: Synthetic adapter

<400> SEQUENCE: 224
caagcagaag acggcatacg agattgttat acgtgactgg agttcagacg tgtgctcttc 60
cgatct 66

<210> SEQ ID NO 225
<211> LENGTH: 66
<212> TYPE: DNA
<213> ORGANISM: Artificial
<220> FEATURE:
<223> OTHER INFORMATION: Synthetic adapter

<400> SEQUENCE: 225
caagcagaag acggcatacg agattcagcg aagtgactgg agttcagacg tgtgctcttc 60
cgatct 66

<210> SEQ ID NO 226
<211> LENGTH: 66
<212> TYPE: DNA
<213> ORGANISM: Artificial
<220> FEATURE:
<223> OTHER INFORMATION: Synthetic adapter

<400> SEQUENCE: 226
caagcagaag acggcatacg agatgtcaag ttgtgactgg agttcagacg tgtgctcttc 60
cgatct 66

<210> SEQ ID NO 227
<211> LENGTH: 66
<212> TYPE: DNA
<213> ORGANISM: Artificial
<220> FEATURE:
<223> OTHER INFORMATION: Synthetic adapter

<400> SEQUENCE: 227
caagcagaag acggcatacg agataggatg tggtgactgg agttcagacg tgtgctcttc 60
cgatct 66

<210> SEQ ID NO 228
<211> LENGTH: 66
<212> TYPE: DNA
<213> ORGANISM: Artificial
<220> FEATURE:
<223> OTHER INFORMATION: Synthetic adapter

<400> SEQUENCE: 228
caagcagaag acggcatacg agatcattcc gagtgactgg agttcagacg tgtgctcttc 60
cgatct 66

<210> SEQ ID NO 229
<211> LENGTH: 66
<212> TYPE: DNA
<213> ORGANISM: Artificial
<220> FEATURE:
<223> OTHER INFORMATION: Synthetic adapter

<400> SEQUENCE: 229
caagcagaag acggcatacg agatacatcc ttgtgactgg agttcagacg tgtgctcttc 60
cgatct 66

<210> SEQ ID NO 230
<211> LENGTH: 33
<212> TYPE: DNA
<213> ORGANISM: Artificial
<220> FEATURE:
<223> OTHER INFORMATION: Synthetic primer

<400> SEQUENCE: 230
tcgtcggcag cgtcagatgt gtataagaga cag 33

<210> SEQ ID NO 231
<211> LENGTH: 34
<212> TYPE: DNA
<213> ORGANISM: Artificial
<220> FEATURE:
<223> OTHER INFORMATION: Synthetic primer

<400> SEQUENCE: 231
agatcggaag agcacacgtc tgaactccag tcac 34

<210> SEQ ID NO 232
<211> LENGTH: 34
<212> TYPE: DNA
<213> ORGANISM: Artificial
<220> FEATURE:
<223> OTHER INFORMATION: Synthetic primer

<400> SEQUENCE: 232
gtgactggag ttcagacgtg tgctcttccg atct 34

<210> SEQ ID NO 233
<211> LENGTH: 8
<212> TYPE: DNA
<213> ORGANISM: Artificial Sequence
<220> FEATURE:
<223> OTHER INFORMATION: Synthetic barcode

<400> SEQUENCE: 233 gaatgagt 8

<210> SEQ ID NO 234
<211> LENGTH: 8
<212> TYPE: DNA
<213> ORGANISM: Artificial Sequence
<220> FEATURE:
<223> OTHER INFORMATION: Synthetic barcode

<400> SEQUENCE: 234 agagatct 8

<210> SEQ ID NO 235
<211> LENGTH: 8
<212> TYPE: DNA
<213> ORGANISM: Artificial Sequence
<220> FEATURE:
<223> OTHER INFORMATION: Synthetic barcode

<400> SEQUENCE: 235 tagactat 8

<210> SEQ ID NO 236
<211> LENGTH: 8
<212> TYPE: DNA
<213> ORGANISM: Artificial Sequence
<220> FEATURE:
<223> OTHER INFORMATION: Synthetic barcode

<400> SEQUENCE: 236 tgctctca 8

<210> SEQ ID NO 237
<211> LENGTH: 8
<212> TYPE: DNA
<213> ORGANISM: Artificial Sequence
<220> FEATURE:
<223> OTHER INFORMATION: Synthetic barcode

<400> SEQUENCE: 237 cggcgtgg 8

<210> SEQ ID NO 238
<211> LENGTH: 8
<212> TYPE: DNA
<213> ORGANISM: Artificial Sequence
<220> FEATURE:
<223> OTHER INFORMATION: Synthetic barcode

<400> SEQUENCE: 238 ctaatgcg 8

<210> SEQ ID NO 239
<211> LENGTH: 8
<212> TYPE: DNA
<213> ORGANISM: Artificial Sequence
<220> FEATURE:
<223> OTHER INFORMATION: Synthetic barcode

<400> SEQUENCE: 239 tagtgaac 8

<210> SEQ ID NO 240
<211> LENGTH: 8

<212> TYPE: DNA
<213> ORGANISM: Artificial Sequence
<220> FEATURE:
<223> OTHER INFORMATION: Synthetic barcode

<400> SEQUENCE: 240 ccggcgtc 8

<210> SEQ ID NO 241
<211> LENGTH: 8
<212> TYPE: DNA
<213> ORGANISM: Artificial Sequence
<220> FEATURE:
<223> OTHER INFORMATION: Synthetic barcode

<400> SEQUENCE: 241 aacattct 8

<210> SEQ ID NO 242
<211> LENGTH: 8
<212> TYPE: DNA
<213> ORGANISM: Artificial Sequence
<220> FEATURE:
<223> OTHER INFORMATION: Synthetic barcode

<400> SEQUENCE: 242 tcgctaca 8

<210> SEQ ID NO 243
<211> LENGTH: 8
<212> TYPE: DNA
<213> ORGANISM: Artificial Sequence
<220> FEATURE:
<223> OTHER INFORMATION: Synthetic barcode

<400> SEQUENCE: 243 gtgttagc 8

<210> SEQ ID NO 244
<211> LENGTH: 8
<212> TYPE: DNA
<213> ORGANISM: Artificial Sequence
<220> FEATURE:
<223> OTHER INFORMATION: Synthetic barcode

<400> SEQUENCE: 244 tgcgacat 8

<210> SEQ ID NO 245
<211> LENGTH: 8
<212> TYPE: DNA
<213> ORGANISM: Artificial Sequence
<220> FEATURE:
<223> OTHER INFORMATION: Synthetic barcode

<400> SEQUENCE: 245 ccgctcag 8

<210> SEQ ID NO 246
<211> LENGTH: 8
<212> TYPE: DNA
<213> ORGANISM: Artificial Sequence
<220> FEATURE:
<223> OTHER INFORMATION: Synthetic barcode

<400> SEQUENCE: 246

-continued

```
gatctgag                                                            8


<210> SEQ ID NO 247
<211> LENGTH: 8
<212> TYPE: DNA
<213> ORGANISM: Artificial Sequence
<220> FEATURE:
<223> OTHER INFORMATION: Synthetic barcode

<400> SEQUENCE: 247

tcgaaccg                                                            8


<210> SEQ ID NO 248
<211> LENGTH: 8
<212> TYPE: DNA
<213> ORGANISM: Artificial Sequence
<220> FEATURE:
<223> OTHER INFORMATION: Synthetic barcode

<400> SEQUENCE: 248

tccacact                                                            8


<210> SEQ ID NO 249
<211> LENGTH: 8
<212> TYPE: DNA
<213> ORGANISM: Artificial Sequence
<220> FEATURE:
<223> OTHER INFORMATION: Synthetic barcode

<400> SEQUENCE: 249

taggcgcg                                                            8


<210> SEQ ID NO 250
<211> LENGTH: 8
<212> TYPE: DNA
<213> ORGANISM: Artificial Sequence
<220> FEATURE:
<223> OTHER INFORMATION: Synthetic barcode

<400> SEQUENCE: 250

attggagc                                                            8


<210> SEQ ID NO 251
<211> LENGTH: 8
<212> TYPE: DNA
<213> ORGANISM: Artificial Sequence
<220> FEATURE:
<223> OTHER INFORMATION: Synthetic barcode

<400> SEQUENCE: 251

gtctgccg                                                            8
```

RNA SEQUENCING METHOD FOR THE ANALYSIS OF B AND T CELL TRANSCRIPTOME IN PHENOTYPICALLY DEFINED B AND T CELL SUBSETS

SEQUENCE LISTING

This application includes as the Sequence Listing the complete contents of the .txt file "2022 Feb. 8 US_adapted_sequence_listing", created Jan. 25, 2022, containing 54,776 bytes, hereby incorporated by reference.

FIELD OF THE INVENTION

The present invention relates to RNA sequencing (RNAseq) method for the analysis of B and T cell transcriptome in phenotypically defined B and T cell subsets, and in particular to single-cell RNA sequencing (scRNAseq) method.

BACKGROUND OF THE INVENTION

Single-cell RNA sequencing (scRNAseq) allows the identification, characterization, and quantification of cell types in a tissue. When focused on the adaptive immune system's T and B cells, scRNAseq carries the potential to track the clonal lineage of each analyzed cell through the unique rearranged sequence of its antigen receptor (TCR or BCR, respectively), and link it to the functional state inferred from transcriptome analysis.

Computational approaches to infer clonality and maturation status (for BCR only) from scRNAseq datasets of T and B cells have been developed, but so far they rely either on data produced by the cumbersome full-length sequencing protocol (Smart-seq2), or on costly additional sequencing of PCR-amplified amplicon libraries from 5'-end scRNAseq protocols (10× GENOMICS (a trademark of Novogene, Inc. for an RNA screening assay)).

While SMART-SEQ2 a full length single cell RNA sequencing protocol developed by Ludwig Institute for Cancer Research, Stockholm, Sweden (or any other full-length plate-based scRNAseq method) allows for a deep analysis of phenotypically defined FACS-sorted cells, it is costly, labor intensive, it does not allow the use of unique molecular identifiers (UMI) to correct for amplification bias during library preparation.

Conversely, while 10× GENOMICS (a trademark of Novogene, Inc. for an RNA screening assay) (or any other droplet-based scRNAseq method) incorporates UMIs, is relatively cheap and easy to perform, it does not allow the precise selection of phenotypically defined cells or the direct reconstruction of BCR and TCR repertoires from scRNAseq reads, and suffers from a low sensitivity.

So there is still a need for a scRNAseq method for cost effective integrative analysis of B and T cell transcriptome and paired BCR and TCR repertoire in phenotypically defined B and T cell subsets.

SUMMARY OF THE INVENTION

The present invention relates to RNA sequencing (RNAseq) method for the analysis of B and T cell transcriptome in phenotypically defined B and T cell subsets. In particular, the present invention relates to single-cell RNA sequencing (scRNAseq) method for the analysis of B and T cell transcriptome in phenotypically defined B and T cell subsets. In particular, the present invention is defined by the claims.

DETAILED DESCRIPTION OF THE INVENTION

The inventors have now developed a FACS-based 5'-end scRNAseq method for cost effective integrative analysis of B and T cell transcriptome and paired BCR and TCR repertoire in phenotypically defined B and T cell subsets. In particular, the method of the present invention includes a reverse transcription step that uses a number of different well specific template switching oligonucleotides (TSO) to introduce a well-specific DNA barcode in the 5'-end of cDNAs.

Template Switching Oligonucleotides of the Present Invention and Uses Thereof for Reverse Transcription:

Accordingly, the first object of the present invention relates to a template switching oligonucleotide (TSO) characterized in that it comprises:

a 5'-terminal PCR handle sequence
a barcode sequence
an Unique Molecular Identifier (UMI) sequence
an insulator sequence and
a 3' terminal sequence consisting of 3 riboguanosine (rG)

In some embodiment, the present invention relates to a template switching oligonucleotide (TSO) characterized in that it comprises, in the order and in succession:

a 5'-terminal PCR handle sequence
a barcode sequence
an Unique Molecular Identifier (UMI) sequence
an insulator sequence and
a 3' terminal sequence consisting of 3 riboguanosine (rG).

As used herein, the term "nucleotide" denotes a sugar, usually ribose or deoxyribose, and a purine or pyrimidine base ("nucleoside"), comprising a phosphate group attached to the sugar. As used herein, the term "pyrimidine nucleoside" or "py" refers to a nucleoside wherein the base component of the nucleoside is a pyrimidine base (e.g., cytosine (C) or thymine (T) or Uracil (U)). Similarly, the term "purine nucleoside" or "pu" refers to a nucleoside wherein the base component of the nucleoside is a purine base (e.g., adenine (A) or guanine (G)).

As used herein, the terms "polynucleotide" and "nucleic acid" are used interchangeably and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs.

As used herein, the term "3' when used directionally, generally refers to a region or position in a polynucleotide or oligonucleotide 3' (downstream) from another region or position in the same polynucleotide or oligonucleotide.

As used herein, the term "5" when used directionally, generally refers to a region or position in a polynucleotide or oligonucleotide 5' (upstream) from another region or position in the same polynucleotide or oligonucleotide.

As used herein, the term "oligonucleotide" refers to short, generally single stranded, generally synthetic polynucleotides that are generally, but not necessarily, less than about 200 nucleotides in length. The oligonucleotides of the present invention can be obtained from existing nucleic acid sources, including genomic or cDNA, but are preferably produced by synthetic methods. In some embodiments each nucleoside unit can encompass various chemical modifications and substitutions as compared to wild-type oligonucleotides, including but not limited to modified nucleoside base and/or modified sugar unit. Examples of chemical modifications are known to the person skilled in the art and are described, for example, in Uhlmann E et al. (1990) Chem. Rev. 90:543; "Protocols for Oligonucleotides and Analogs". Nucleotides, their derivatives and the synthesis thereof is described in Habermehl et al., Naturstoffchemie, 3rd edition, Springer, 2008.

As used herein, the term "template switch oligonucleotide" or "TSO" refers to an oligonucleotide that comprises a portion (or region) that is hybridizable to a template at a location 5' to the termination site of primer extension and that is capable of effecting a template switch in the process of primer extension by a DNA polymerase, generally due to a sequence that is not hybridized to the template.

As used herein, the term "PCR handle sequence" refers to any nucleic acid sequence that will allow PCR amplification. Typically, said sequence comprises 15, 16, 17, 18, 19, 20, 21, 22, 23, 24 or 25 nucleotides. In some embodiments, the sequence comprises 21 nucleotides. In some embodiments, the sequence consists of AGACGTGTGCTCTTCCGATCT (SEQ ID NO: 1).

As used herein, the term "nucleic acid barcode sequence" refers to a nucleic acid having a sequence which can be used to identify and/or distinguish one or more first molecules to which the nucleic acid barcode is conjugated from one or more second molecules. Nucleic acid barcode sequences are typically short, e.g., about 5 to 20 bases in length, and may be conjugated to one or more target molecules of interest or amplification products thereof. Nucleic acid barcode sequences may be single or double stranded.

In some embodiments, the barcode sequence is a DNA barcode sequence.

In some embodiments, the barcode sequence is selected from the group consisting of:

| Name | Sequence | SEQ ID NO: |
|---|---|---|
| A1 | CGTCTAAT | 2 |
| A2 | AGACTCGT | 3 |
| A3 | GCACGTCA | 4 |
| A4 | TCAACGAC | 5 |
| A5 | ATTTAGCG | 6 |
| A6 | ATACAGAC | 7 |
| A7 | TGCGTAGG | 8 |
| A8 | TGGAGCTC | 9 |
| A9 | TGAATACC | 10 |
| A10 | TCTCACAC | 11 |
| A11 | TACTGGTA | 12 |
| A12 | ACGATAGG | 13 |
| B1 | GATGTCGA | 14 |
| B2 | TTACGGGT | 15 |
| B3 | CACAGCAT | 16 |
| B3' | GAATGAGT | 233 |

-continued

| Name | Sequence | SEQ ID NO: |
|---|---|---|
| B4 | CTTTGACA | 17 |
| B5 | CCTTCAAG | 18 |
| B5' | AGAGATCT | 234 |
| B6 | GAGTCCTG | 19 |
| B7 | CACACTGA | 20 |
| B8 | GTTACAGG | 21 |
| B9 | GGACCTTT | 22 |
| B10 | TTCCGTTC | 23 |
| B10' | TAGACTAT | 235 |
| B11 | ACTGTTTG | 24 |
| B12 | AAGTGGCT | 25 |
| C1 | CTGTACAA | 26 |
| C1' | TGCTCTCA | 236 |
| C2 | CGCAAAGT | 27 |
| C2' | CGGCGTGG | 237 |
| C3 | GTGCATGA | 28 |
| C4 | GTCATTAG | 29 |
| C5 | AGCTCCTT | 30 |
| C6 | TCACCCGA | 31 |
| C7 | GTTGCCAC | 32 |
| C8 | TGTACCAA | 33 |
| C8' | CTAATGCG | 238 |
| C9 | AACGAGGT | 34 |
| C10 | AGCCACCA | 35 |
| C11 | GGTAATCA | 36 |
| C11' | TAGTGAAC | 239 |
| C12 | CCAGTCCA | 37 |
| D1 | ACCTCAGC | 38 |
| D2 | GGTGGACT | 39 |
| D3 | GACAAACC | 40 |
| D3' | CCGGCGTC | 240 |
| D4 | TAACTCCG | 41 |
| D5 | ACACCGTG | 42 |
| D6 | GTAGAACG | 43 |
| D7 | GGATTGAC | 44 |
| D8 | ACGTATCC | 45 |
| D9 | TTCGGAAA | 46 |
| D10 | AGTTGTGT | 47 |

-continued

| Name | Sequence | SEQ ID NO: |
|---|---|---|
| D11 | AAGCACAT | 48 |
| D12 | CTGTCATT | 49 |
| E1 | GTCCTATA | 50 |
| E1' | AACATTCT | 241 |
| E2 | CTACGCTG | 51 |
| E3 | GGGATTGT | 52 |
| E4 | TGATGTAG | 53 |
| E5 | TTCGCTGT | 54 |
| E6 | GAAGACTT | 55 |
| E7 | TCTGGGCA | 56 |
| E8 | CAACTAGA | 57 |
| E8' | TCGCTACA | 242 |
| E9 | CCATGGGA | 58 |
| E9' | GTGTTAGC | 243 |
| E10 | ATGCGACG | 59 |
| E11 | GAGGGTAG | 60 |
| E12 | CGGGTGAA | 61 |
| F1 | GCCATCTT | 62 |
| F2 | GCATAATC | 63 |
| F2' | TGCGACAT | 244 |
| F3 | TCTATGGT | 64 |
| F4 | AGGACTTA | 65 |
| F5 | CGTGATTC | 66 |
| F5' | CCGCTCAG | 245 |
| F6 | ACTAGCGA | 67 |
| F7 | GTAACTCC | 68 |
| F8 | CGGAAGTG | 69 |
| F9 | CCGAGTAC | 70 |
| F10 | GACGCAAT | 71 |
| F10' | GATCTGAG | 246 |
| F11 | ACCTGGAG | 72 |
| F12 | CATGGGTT | 73 |
| G1 | ATTCCTAG | 74 |
| G2 | AATCATGC | 75 |
| G2' | TCGAACCG | 247 |
| G3 | GCTTCCCT | 76 |
| G3' | TCCACACT | 248 |
| G4 | AGGTAAAG | 77 |
| G5 | CCACAACT | 78 |

-continued

| Name | Sequence | SEQ ID NO: |
|---|---|---|
| G5' | TAGGCGCG | 249 |
| G6 | ACAGGCAT | 79 |
| G7 | TTTGTGTC | 80 |
| G8 | TGAGCATA | 81 |
| G9 | TTAGACGC | 82 |
| G10 | CGCTTGCT | 83 |
| G11 | AGTCTGCC | 84 |
| G11' | ATTGGAGC | 250 |
| G12 | CATAGTCG | 85 |
| H1 | TCTTGCTG | 86 |
| H2 | GGGACAAC | 87 |
| H3 | ATATTCCC | 88 |
| H4 | TGTTAAGC | 89 |
| H5 | TACGCCTC | 90 |
| H6 | CACTTATC | 91 |
| H7 | ACCGCTAA | 92 |
| H8 | TAAGGTCC | 93 |
| H9 | GAAAGGTG | 94 |
| H10 | ACGTTGTA | 95 |
| H11 | GCAGAGAA | 96 |
| H11' | GTCTGCCG | 251 |
| H12 | GCATTTGG | 97 |

As used herein, the term "unique molecular identifier (UMI) sequence" or "UM sequence" refers to a nucleic acid having a sequence which can be used to identify and/or distinguish one or more first molecules to which the UMI is conjugated from one or more second molecules. UMIs are typically short, e.g., about 4 to 10 bases in length, and typical comprises 4, 5, 6, 7, 8, 9 or 10 nucleotides. According to the present invention the UMI sequence consists of a random sequence. As used herein, the term "random sequence" is defined as deoxyribonucleotide, ribonucleotide or mixed deoxyribo/ribonucleotide sequence which contains in each nucleotide position any natural or modified nucleotide. In some embodiments, the UMI sequences consists of 5 nucleotides long random sequence NNNNN wherein N denotes any nucleotide.

As used herein, the term "insulator sequence" refers to any sequence that consists of 3, 4, 5, 6, 7 nucleotides. In some embodiments, the sequence consists of TATA (SEQ ID NO:98).

As used herein, the term "riboguanosine" or "rG" has its general meaning in the art and refers to a purine deoxyribonucleoside, and is one of the four standard nucleosides that compose an RNA molecule. The presence of the —OH group at the 2'-position of the ribose results in RNA being less stable to DNA (which lacks —OH groups at this position), because this 2'-hydroxyl group can chemically attack the adjacent phosphodiester bond in the sugar-phosphate backbone of RNA, leading to cleavage of the backbone structure. rG forms a Watson-Crick base pair with rC (ribocytosine/cytosine) in RNA duplexes, or dC (deoxyribocytosine) in RNA-DNA duplexes.

In some embodiments, the TSO of the present invention consists of the sequence AGACGTGTGCTCTTCCGATCTXXXXXXXXNNNNNTATArGrGrG wherein the sequence XXXXXXXX represents the DNA barcode sequences and the sequence NNNNN represents the UMI sequence.

In some embodiments, the TSO of the present invention consists of a sequence selected from the group consisting of:

| Name | Sequence | SEQ ID NO: 1 |
|---|---|---|
| TSO_1_A1_U5TATA_PM | AGACGTGTGCTCTTCCGATCTCGTCTAATNNNNNTATArGrGrG | 99 |
| TSO_2_A2_U5TATA_PM | AGACGTGTGCTCTTCCGATCTAGACTCGTNNNNNTATArGrGrG | 100 |
| TSO_3_A3_U5TATA_PM | AGACGTGTGCTCTTCCGATCTGCACGTCANNNNNTATArGrGrG | 101 |
| TSO_4_A4_U5TATA_PM | AGACGTGTGCTCTTCCGATCTTCAACGACNNNNNTATArGrGrG | 102 |
| TSO_5_A5_U5TATA_PM | AGACGTGTGCTCTTCCGATCTATTTAGCGNNNNNTATArGrGrG | 103 |
| TSO_6_A6_U5TATA_PM | AGACGTGTGCTCTTCCGATCTATACAGACNNNNNTATArGrGrG | 104 |
| TSO_7_A7_U5TATA_PM | AGACGTGTGCTCTTCCGATCTTGCGTAGGNNNNNTATArGrGrG | 105 |
| TSO_8_A8_U5TATA_PM | AGACGTGTGCTCTTCCGATCTTGGAGCTCNNNNNTATArGrGrG | 106 |
| TSO_9_A9_U5TATA_PM | AGACGTGTGCTCTTCCGATCTTGAATACCNNNNNTATArGrGrG | 107 |
| TSO_10_A10_U5TATA_PM | AGACGTGTGCTCTTCCGATCTTCTCACACNNNNNTATArGrGrG | 108 |
| TSO_11_A11_U5TATA_PM | AGACGTGTGCTCTTCCGATCTTACTGGTANNNNNTATArGrGrG | 109 |
| TSO_12_A12_U5TATA_PM | AGACGTGTGCTCTTCCGATCTACGATAGGNNNNNTATArGrGrG | 110 |
| TSO_13_B1_U5TATA_PM | AGACGTGTGCTCTTCCGATCTGATGTCGANNNNNTATArGrGrG | 111 |
| TSO_14_B2_U5TATA_PM | AGACGTGTGCTCTTCCGATCTTTACGGGTNNNNNTATArGrGrG | 112 |
| TSO_15_97_B3_U5TATA_PM | AGACGTGTGCTCTTCCGATCTGAATGAGTNNNNNTATArGrGrG | 113 |
| TSO_16_B4_U5TATA_PM | AGACGTGTGCTCTTCCGATCTCTTTGACANNNNNTATArGrGrG | 114 |
| TSO_17_98_B5_U5TATA_PM | AGACGTGTGCTCTTCCGATCTAGAGATCTNNNNNTATArGrGrG | 115 |
| TSO_18_B6_U5TATA_PM | AGACGTGTGCTCTTCCGATCTGAGTCCTGNNNNNTATArGrGrG | 116 |
| TSO_19_B7_U5TATA_PM | AGACGTGTGCTCTTCCGATCTCACACTGANNNNNTATArGrGrG | 117 |
| TSO_20_B8_U5TATA_PM | AGACGTGTGCTCTTCCGATCTGTTACAGGNNNNNTATArGrGrG | 118 |
| TSO_21_B9_U5TATA_PM | AGACGTGTGCTCTTCCGATCTGGACCTTTNNNNNTATArGrGrG | 119 |
| TSO_22_99_B10_U5TATA_PM | AGACGTGTGCTCTTCCGATCTTAGACTATNNNNNTATArGrGrG | 120 |
| TSO_23_B11_U5TATA_PM | AGACGTGTGCTCTTCCGATCTACTGTTTGNNNNNTATArGrGrG | 121 |

-continued

| Name | Sequence | SEQ ID NO: 1 |
|---|---|---|
| TSO_24_B12_U5TATA_PM | AGACGTGTGCTCTTCCGATCTAAGTGGCTNNNNNTATArG rGrG | 122 |
| TSO_25_100_C1_U5TATA_PM | AGACGTGTGCTCTTCCGATCTTGCTCTCANNNNNTATArG rGrG | 123 |
| TSO_26_104_C2_U5TATA_PM | AGACGTGTGCTCTTCCGATCTCGGCGTGGNNNNNTATArG rGrG | 124 |
| TSO_27_C3_U5TATA_PM | AGACGTGTGCTCTTCCGATCTGTGCATGANNNNNTATArG rGrG | 125 |
| TSO_28_C4_U5TATA_PM | AGACGTGTGCTCTTCCGATCTGTCATTAGNNNNNTATArG rGrG | 126 |
| TSO_29_C5_U5TATA_PM | AGACGTGTGCTCTTCCGATCTAGCTCCTTNNNNNTATArG rGrG | 127 |
| TSO_30_C6_U5TATA_PM | AGACGTGTGCTCTTCCGATCTTCACCCGANNNNNTATArG rGrG | 128 |
| TSO_31_C7_U5TATA_PM | AGACGTGTGCTCTTCCGATCTGTTGCCACNNNNNTATArG rGrG | 129 |
| TSO_32_106_C8_U5TATA_PM | AGACGTGTGCTCTTCCGATCTCTAATGCGNNNNNTATArG rGrG | 130 |
| TSO_33_C9_U5TATA_PM | AGACGTGTGCTCTTCCGATCTAACGAGGTNNNNNTATArG rGrG | 131 |
| TSO_34_C10_U5TATA_PM | AGACGTGTGCTCTTCCGATCTAGCCACCANNNNNTATArG rGrG | 132 |
| TSO_35_107_C11_U5TATA_PM | AGACGTGTGCTCTTCCGATCTTAGTGAACNNNNNTATArG rGrG | 133 |
| TSO_36_C12_U5TATA_PM | AGACGTGTGCTCTTCCGATCTCCAGTCCANNNNNTATArG rGrG | 134 |
| TSO_37_D1_U5TATA_PM | AGACGTGTGCTCTTCCGATCTACCTCAGCNNNNNTATArG rGrG | 135 |
| TSO_38_D2_U5TATA_PM | AGACGTGTGCTCTTCCGATCTGGTGGACTNNNNNTATArG rGrG | 136 |
| TSO_39_108_D3_U5TATA_PM | AGACGTGTGCTCTTCCGATCTCCGGCGTCNNNNNTATArG rGrG | 137 |
| TSO_40_D4_U5TATA_PM | AGACGTGTGCTCTTCCGATCTTAACTCCGNNNNNTATArG rGrG | 138 |
| TSO_41_D5_U5TATA_PM | AGACGTGTGCTCTTCCGATCTACACCGTGNNNNNTATArG rGrG | 139 |
| TSO_42_D6_U5TATA_PM | AGACGTGTGCTCTTCCGATCTGTAGAACGNNNNNTATArG rGrG | 140 |
| TSO_43_D7_U5TATA_PM | AGACGTGTGCTCTTCCGATCTGGATTGACNNNNNTATArG rGrG | 141 |
| TSO_44_D8_U5TATA_PM | AGACGTGTGCTCTTCCGATCTACGTATCCNNNNNTATArG rGrG | 142 |
| TSO_45_D9_U5TATA_PM | AGACGTGTGCTCTTCCGATCTTTCGGAAANNNNNTATArG rGrG | 143 |
| TSO_46_D10_U5TATA_PM | AGACGTGTGCTCTTCCGATCTAGTTGTGTNNNNNTATArG rGrG | 144 |
| TSO_47_D11_U5TATA_PM | AGACGTGTGCTCTTCCGATCTAAGCACATNNNNNTATArG rGrG | 145 |

-continued

| Name | Sequence | SEQ ID NO: 1 |
|---|---|---|
| TSO_48_D12_U5TATA_PM | AGACGTGTGCTCTTCCGATCTCTGTCATTNNNNNTATArG rGrG | 146 |
| TSO_49_109_E1_U5TATA_PM | AGACGTGTGCTCTTCCGATCTAACATTCTNNNNNTATArG rGrG | 147 |
| TSO_50_E2_U5TATA_PM | AGACGTGTGCTCTTCCGATCTCTACGCTGNNNNNTATArG rGrG | 148 |
| TSO_51_E3_U5TATA_PM | AGACGTGTGCTCTTCCGATCTGGGATTGTNNNNNTATArG rGrG | 149 |
| TSO_52_E4_U5TATA_PM | AGACGTGTGCTCTTCCGATCTTGATGTAGNNNNNTATArG rGrG | 150 |
| TSO_53_E5_U5TATA_PM | AGACGTGTGCTCTTCCGATCTTTCGCTGTNNNNNTATArG rGrG | 151 |
| TSO_54_E6_U5TATA_PM | AGACGTGTGCTCTTCCGATCTGAAGACTTNNNNNTATArG rGrG | 152 |
| TSO_55_E7_U5TATA_PM | AGACGTGTGCTCTTCCGATCTTCTGGGCANNNNNTATArG rGrG | 153 |
| TSO_56_110_E8_U5TATA_PM | AGACGTGTGCTCTTCCGATCTTCGCTACANNNNNTATArG rGrG | 154 |
| TSO_57_111_E9_U5TATA_PM | AGACGTGTGCTCTTCCGATCTGTGTTAGCNNNNNTATArG rGrG | 155 |
| TSO_58_E10_U5TATA_PM | AGACGTGTGCTCTTCCGATCTATGCGACGNNNNNTATArG rGrG | 156 |
| TSO_59_E11_U5TATA_PM | AGACGTGTGCTCTTCCGATCTGAGGGTAGNNNNNTATArG rGrG | 157 |
| TSO_60_E12_U5TATA_PM | AGACGTGTGCTCTTCCGATCTCGGGTGAANNNNNTATArG rGrG | 158 |
| TSO_61_F1_U5TATA_PM | AGACGTGTGCTCTTCCGATCTGCCATCTTNNNNNTATArG rGrG | 159 |
| TSO_62_112_F2_U5TATA_PM | AGACGTGTGCTCTTCCGATCTTGCGACATNNNNNTATArG rGrG | 160 |
| TSO_63_F3_U5TATA_PM | AGACGTGTGCTCTTCCGATCTTCTATGGTNNNNNTATArG rGrG | 161 |
| TSO_64_F4_U5TATA_PM | AGACGTGTGCTCTTCCGATCTAGGACTTANNNNNTATArG rGrG | 162 |
| TSO_65_113_F5_U5TATA_PM | AGACGTGTGCTCTTCCGATCTCCGCTCAGNNNNNTATArG rGrG | 163 |
| TSO_66_F6_U5TATA_PM | AGACGTGTGCTCTTCCGATCTACTAGCGANNNNNTATArG rGrG | 164 |
| TSO_67_F7_U5TATA_PM | AGACGTGTGCTCTTCCGATCTGTAACTCCNNNNNTATArG rGrG | 165 |
| TSO_68_F8_U5TATA_PM | AGACGTGTGCTCTTCCGATCTCGGAAGTGNNNNNTATArG rGrG | 166 |
| TSO_69_F9_U5TATA_PM | AGACGTGTGCTCTTCCGATCTCCGAGTACNNNNNTATArG rGrG | 167 |
| TSO_70_114_F10_U5TATA_PM | AGACGTGTGCTCTTCCGATCTGATCTGAGNNNNNTATArG rGrG | 168 |
| TSO_71_F11_U5TATA_PM | AGACGTGTGCTCTTCCGATCTACCTGGAGNNNNNTATArG rGrG | 169 |

-continued

| Name | Sequence | SEQ ID NO: 1 |
|---|---|---|
| TSO_72_F12_U5TATA_PM | AGACGTGTGCTCTTCCGATCTCATGGGTTNNNNNTATArG rGrG | 170 |
| TSO_73_G1_U5TATA_PM | AGACGTGTGCTCTTCCGATCTATTCCTAGNNNNNTATArG rGrG | 171 |
| TSO_74_115_G2_U5TATA_PM | AGACGTGTGCTCTTCCGATCTTCGAACCGNNNNNTATArG rGrG | 172 |
| TSO_75_116_G3_U5TATA_PM | AGACGTGTGCTCTTCCGATCTTCCACACTNNNNNTATArG rGrG | 173 |
| TSO_76_G4_U5TATA_PM | AGACGTGTGCTCTTCCGATCTAGGTAAAGNNNNNTATArG rGrG | 174 |
| TSO_77_118_G5_U5TATA_PM | AGACGTGTGCTCTTCCGATCTTAGGCGCGNNNNNTATArG rGrG | 175 |
| TSO_78_G6_U5TATA_PM | AGACGTGTGCTCTTCCGATCTACAGGCATNNNNNTATArG rGrG | 176 |
| TSO_79_G7_U5TATA_PM | AGACGTGTGCTCTTCCGATCTTTTGTGTCNNNNNTATArG rGrG | 177 |
| TSO_80_G8_U5TATA_PM | AGACGTGTGCTCTTCCGATCTTGAGCATANNNNNTATArG rGrG | 178 |
| TSO_81_G9_U5TATA_PM | AGACGTGTGCTCTTCCGATCTTTAGACGCNNNNNTATArG rGrG | 179 |
| TSO_82_G10_U5TATA_PM | AGACGTGTGCTCTTCCGATCTCGCTTGCTNNNNNTATArG rGrG | 180 |
| TSO_83_119_G11_U5TATA_PM | AGACGTGTGCTCTTCCGATCTATTGGAGCNNNNNTATArG rGrG | 181 |
| TSO_84_G12_U5TATA_PM | AGACGTGTGCTCTTCCGATCTCATAGTCGNNNNNTATArG rGrG | 182 |
| TSO_85_H1_U5TATA_PM | AGACGTGTGCTCTTCCGATCTTCTTGCTGNNNNNTATArG rGrG | 183 |
| TSO_86_H2_U5TATA_PM | AGACGTGTGCTCTTCCGATCTGGGACAACNNNNNTATArG rGrG | 184 |
| TSO_87_H3_U5TATA_PM | AGACGTGTGCTCTTCCGATCTATATTCCCNNNNNTATArG rGrG | 185 |
| TSO_88_H4_U5TATA_PM | AGACGTGTGCTCTTCCGATCTTGTTAAGCNNNNNTATArG rGrG | 186 |
| TSO_89_H5_U5TATA_PM | AGACGTGTGCTCTTCCGATCTTACGCCTCNNNNNTATArG rGrG | 187 |
| TSO_90_H6_U5TATA_PM | AGACGTGTGCTCTTCCGATCTCACTTATCNNNNNTATArG rGrG | 188 |
| TSO_91_H7_U5TATA_PM | AGACGTGTGCTCTTCCGATCTACCGCTAANNNNNTATArG rGrG | 189 |
| TSO_92_H8_U5TATA_PM | AGACGTGTGCTCTTCCGATCTTAAGGTCCNNNNNTATArG rGrG | 190 |
| TSO_93_H9_U5TATA_PM | AGACGTGTGCTCTTCCGATCTGAAAGGTGNNNNNTATArG rGrG | 191 |
| TSO_94_H10_U5TATA_PM | AGACGTGTGCTCTTCCGATCTACGTTGTANNNNNTATArG rGrG | 192 |
| TSO_95_120_H11_U5TATA_PM | AGACGTGTGCTCTTCCGATCTGTCTGCCGNNNNNTATArG rGrG | 193 |
| TSO_96_H12_U5TATA_PM | AGACGTGTGCTCTTCCGATCTGCATTTGGNNNNNTATArG rGrG | 194 |

A further object of the present invention relates to a method for preparing DNA that is complementary to an RNA molecule (i.e. a cDNA), the method comprising conducting a reverse transcription reaction in the presence of a template switching oligonucleotide (TSO) of the present invention.

According to the present invention, the TSO allow template switching. As used herein, the term "template switching" reaction refers to a process of template-dependent synthesis of the complementary strand by a DNA polymerase using two templates in consecutive order and which are not covalently linked to each other by phosphodiester bonds. The synthesized complementary strand will be a single continuous strand complementary to both templates. Typically, the first template is polyA+RNA and the second template is a template switching or "CAP switch" oligonucleotide.

As used herein, the term "reverse transcriptase" is defined as any DNA polymerase possessing reverse transcriptase activity which can be used for first-strand cDNA synthesis using polyA+RNA or total RNA as a template. Examples of reverse transcriptases that can be used in the methods of the present invention include the DNA polymerases derived from organisms such as thermophilic bacteria and *archaebacteria*, retroviruses, yeast, *Neurospora, Drosophila*, primates and rodents. Preferably, the DNA polymerase is isolated from Moloney murine leukemia virus (M-MLV) (U.S. Pat. No. 4,943,531) or M-MLV reverse transcriptase lacking RNaseH activity (U.S. Pat. No. 5,405,776), human T-cell leukemia virus type I (HTLV-I), bovine leukemia virus (BLV), Rous sarcoma virus (RSV), human immunodeficiency virus (HIV) or *Thermus aquaticus* (Taq) or *Thermus thermophilus* (Tth) (U.S. Pat. No. 5,322,770). Other examples include, MMLV-related reverse transcriptases lacking RNase H activity such as SUPER-SCRIPT II (Invitrogen), POWER SCRIPT (BD Biosciences) and SMART SCRIBE (Clontech). These DNA polymerases may be isolated from an organism itself or, in some cases, obtained commercially. reverse transcriptases useful with the subject invention can also be obtained from cells expressing cloned genes encoding the polymerase.

Typically, reverse transcription reaction is carried out with a thermal cycler in the presence of adequate amounts of other components necessary to perform the reaction, for example, deoxyribonucleoside triphosphates ATP, CTP, GTP and TTP, Mg2+, optimal buffer. In some embodiments, the reaction is performed in presence of methyl group donor such as betaine. According to the invention a "thermal cycler" is a laboratory apparatus or device for carrying out thermal cycles with regard to a reaction process, especially a polymerase chain reaction. The thermal cycler is capable of raising and lowering the temperature of an environment in which micro-environments are provided in discrete, predetermined steps. In some embodiments, the reaction is carried out by incubating at 42° C. for 90 min, followed by 10 cycles of (50° C. for 2 min, 42° C. for 2 min), followed by RT inactivation by incubation at 70° C. for 15 min.

RNA Sequencing (RNAseg) Methods of the Present Invention:

The TSO and reverse transcription method of the present invention are suitable for use in a RNA sequencing (RNAseq) method.

Accordingly, a further object of the present invention relates to a RNA sequencing method comprising the steps of:

A) providing RNA sample
B) reverse transcription (RT) of the RNA molecules
D) amplification of the cDNAs obtained at step C)
E) cDNA pooling and purification
F) preparation of a cDNA library, and
G) sequencing said cDNA library As used herein, the term "RNA sample" refers to a sample comprising RNA molecules from large populations of cells. The RNA samples includes, but are not limited to, total RNA and/or messager RNA (mRNA).

In some embodiment, the RNA molecules is mRNA molecules.

In some embodiment, the RNAseq method is a single-cell RNA sequencing method.

Thus, the TSO and reverse transcription method of the present invention are suitable for use in a single-cell RNA sequencing (scRNAseq) method.

Accordingly, a further object of the present invention relates to a single-cell RNA sequencing method comprising the steps of:

A) isolation of single cells
B) lysis of the singles cells and extraction of the RNA molecules,
C) reverse transcription (RT) of said RNA molecules
D) amplification of the cDNAs obtained at step C)
E) cDNA pooling and purification
F) preparation of a cDNA library, and
G) sequencing said cDNA library The embodiments of said steps are described as follows:

A) Isolation of Single Cells

The step consists in isolating a single cell into a single container.

The scRNAseq method of the present invention can be applied to any type of cells. However the method can be suitably applied to B cells and T cells, in particularly, for cost effective integrative analysis of B and T cell transcriptome and paired BCR and TCR repertoire.

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes by the presence of a B-cell receptor on the cell surface. In some embodiments, the B cell is a memory B cell. In some embodiments, the B cell is a regulatory B cell. A "regulatory B cell" (Breg) is a B cell that suppresses the immune response. Breg cells can suppress T cell activation either directly or indirectly, and may also suppress antigen presenting cells, other innate immune cells, or other B cells. Breg cells can be CD1dhiCD5+ or express a number of other B cell markers and/or belong to other B cell subsets. These cells can also secrete IL-10. Breg cells also express TIM-1, such as TIM-1+CD19+B cells. B-cells also include, for example, plasma B cells, memory B cells, B1 cells, B2 cells, marginal-zone B cells, and follicular B cells. Exemplary B cell surface markers include but are not limited to the CD10, CD19, CD20, CD21, CD22, CD23, CD24, CD37, CD53, CD72, CD73, CD74, CDw75, CDw76, CD77, CDw78, CD79a, CD79b, CD80, CD81, CD82, CD83, CDw84, CD85 and CD86 leukocyte surface markers. The B cell surface marker of particular interest is preferentially expressed on B cells compared to other non-B cell tissues of a mammal. In one embodiment, the marker is one like CD20 or CD19, which is found on B cells throughout differentiation of the lineage from the stem cell stage up to a point just prior to terminal differentiation into plasma cells.

As used herein, the term "T cell," refers to a type of lymphocytes that play an important role in cell-mediated immunity and are distinguished from other lymphocytes, such as B cells, by the presence of a T-cell receptor on the cell surface. Several subsets of T cells have been described and typically include helper T cells (e.g., Th1, Th2, Th9 and Th17 cells), cytotoxic T cells, memory T cells, regulatory/ suppressor T cells (Treg cells), natural killer T cells, [gamma/delta] T cells, and/or autoaggressive T cells (e.g., TH40 cells), unless otherwise indicated by context. In some embodiments, the term "T cell" refers specifically to a helper T cell. In some embodiments, the term "T cell" refers more specifically to a TH17 cell (i.e., a T cell that secretes IL-17). In some embodiments, the term "T ell" refers to a Treg cell.

As used herein, the term "CD4+ T cell" as used herein refers to T helper cells, which either orchestrate the activation of macrophages and CD8+ T cells (Th-1 cells), the production of antibodies by B cells (Th-2 cells) or which have been thought to play an essential role in autoimmune diseases (Th-17 cells). In addition, the term "CD4+ T cells" also refers to regulatory T cells, which represent approximately 10% of the total population of CD4+ T cells. Regulatory T cells play an essential role in the dampening of immune responses, in the prevention of autoimmune diseases and in oral tolerance. The terms "natural regulatory T cells" or "regulatory T cells" as used herein refer to Treg, Th3 and Tr1 cells. Treg are characterized by the expression of surface markers CD4, CD25, CTLA4 and the transcription factor Foxp3. Th3 and Tr1 cells are CD4+ T cells, which are characterized by the expression of TGF-β (Th3 cells) or IL-10 (Tr1 cells), respectively.

As used herein, the term "CD8+ T cell" has its general meaning in the art and refers to a subset of T cells which express CD8 on their surface. They are MHC class I-restricted, and function as cytotoxic T cells. "CD8+ T cells" are also called cytotoxic T lymphocytes (CTL), T-killer cells, cytolytic T cells, or killer T cells. CD8 antigens are members of the immunoglobulin supergene family and are associative recognition elements in major histocompatibility complex class I-restricted interactions.

As used herein, the term "regulatory T cells" or "Treg cells" refers to cells that suppress, inhibit or prevent T cells activity, in particular cytotoxic activity of T CD8+ cells. Regulatory T cells include i) thymus-derived Treg cells (tTreg, previously referred as "natural Treg cells") and ii) peripherally-derived Treg cells (pTreg, previously referred as "induced Treg cells"). As used herein, tTregs have the following phenotype at rest CD4+CD25+FoxP3+. pTreg cells include, for example, Tr1 cells, TGF-β secreting Th3 cells, regulatory NKT cells, regulatory γδ T cells, regulatory CD8+ T cells, and double negative regulatory T cells. The term "Tr1 cells" as used herein refers to cells having the following phenotype at rest: CD4+CD25−CD127−, and the following phenotype when activated: CD4+CD25+CD127−. Tr1 cells, Type 1 T regulatory cells (Type 1 Treg) and IL-10 producing Treg are used herein with the same meaning. In one embodiment, Tr1 cells may be characterized, in part, by their unique cytokine profile: they produce IL-10, and IFN-gamma, but little or no IL-4 or IL-2. In one embodiment, Tr1 cells are also capable of producing IL-13 upon activation. The term "Th3 cells" as used herein refers to cells having the following phenotype CD4+FoxP3+ and capable of secreting high levels TGF-β upon activation, low amounts of IL-4 and IL-10 and no IFN-γ or IL-2. These cells are TGF-β derived. The term "regulatory NKT cells" as used herein refers to cells having the following phenotype at rest CD161+CD56+ CD16+ and expressing a Va24/VB11 TCR. The term "regulatory CD8+ T cells" as used herein refers to cells having the following phenotype at rest CD8+CD122+ and capable of secreting high levels of IL-10 upon activation. The term "double negative regulatory T cells" as used herein refers to cells having the following phenotype at rest TCRαβ+CD4− CD8−. The term "γδ T cells" as used herein refers to T lymphocytes that express the [gamma] [delta] heterodimer of the TCR. Unlike the [alpha] [beta] T lymphocytes, they recognize non-peptide antigens via a mechanism independent of presentation by MHC molecules. Two populations of γδ T cells may be described: the yd T lymphocytes with the V γ9V δ2 receptor, which represent the majority population in peripheral blood and the γδ T lymphocytes with the V δ1 receptor, which represent the majority population in the mucosa and have only a very limited presence in peripheral blood. V γ9V δ2 T lymphocytes are known to be involved in the immune response against intracellular pathogens and hematological diseases.

Typically, the cells, particular B cells and T cells as above descried are isolated by cell sorting. As used herein, the term "cell sorting" is used to refer to a method by which cells are mixed a binding partner (e.g., a fluorescently detectable antibody) in solution. According to the invention, any conventional cell sorting method may be used. Fluorescence-activated cell sorting (FACS) is an example of a cell sorting method. As used herein, the term "fluorescence activated cell sorting" or "FACS" refers to a method by which the individual cells of a sample are analyzed and sorted according to their optical properties (e.g., light absorbance, light scattering and fluorescence properties, etc.) as they pass in a narrow stream in single file through a laser beam. Fluorescence-activated cell sorting is a specialized type of flow cytometry. It provides a method for sorting a heterogeneous mixture of biological cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest. In a typical FACS system, the cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Just before the stream breaks into droplets the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement and the opposite charge is trapped on the droplet as it breaks from the stream. The charged droplets then fall through an electrostatic deflection system that diverts droplets into containers based upon their charge. In some systems the charge is applied directly to the stream and the droplet breaking off retains charge of the same sign as the stream. The stream is then returned to neutral after the droplet breaks off. The fluorescent labels for FACS technique depend on the lamp or laser used to excite the fluorochromes and on the detectors available. The most commonly available lasers on single laser machines are blue argon lasers (488 nm). Fluorescent labels workable for this kind of lasers include, but not limited to, 1) for green fluorescence (usually labelled FL1): FITC, ALEXA FLUOR 488 (AF 488) a fluorescent dye, GFP, CFSE, CFDA-SE, and DyLight 488; 2) for orange fluorescence (usually FL2): PE, and PI; 3) for red fluorescence (usually FL3): PerCP, PE-ALEXA FLUOR 700 (PR- AF 700) a fluorescent dye, PE-Cy5 (TRI-COLOR a fluorescent dye), and PE-Cy5.5; and 4) for infra-red fluorescence (usually FL4; in some FACS machines): PE-ALEXA FLUOR 750 (PR-AF 750) a fluorescent dye, and PE-Cy7. Other lasers and their corresponding fluorescent labels include, but are not limited to, 1) red diode lasers (635 nm): Allophycocyanin (APC), APC-Cy7, ALEXA FLUOR 700 (AF 770) a fluorescent dye, Cy5, and Draq-5; and 2) violet lasers (405 nm): PACIFIC ORANGE (a fluorescent dye from THERMO-FISHER), Amine Aqua, PACIFIC BLUE (a fluorescent dye from THERMO-FISHER), 4,6-diamidino-2-phenylindole (DAPI), and ALEXA FLUOR 405 (AF 405) a fluorescent dye.

Accordingly, FACS typically involves uses of a panel of binding partners specific for some cell surface markers of interest (e.g. BCR, CD19 or CD20 for B cells and TCR, CD4, CD8, CD25 for T cells). The binding partners are thus conjugated to the fluorescent labels as above described. The binding partners may be antibodies that may be polyclonal or monoclonal, preferably monoclonal. In another embodiment, the binding partners may be a set of aptamers. Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies of the invention or a fragment thereof can be prepared and isolated using any technique that provides for the production of antibody molecules by continuous cell lines in culture. Techniques for production and isolation include but are not limited to the hybridoma technique originally; the human B-cell hybridoma technique; and the EBV-hybridoma technique.

Finally, once the single cells are sorted, they are individually deposited in a multi-well container. Preferably, the container consists of a 96-well plate. In some embodiments, several 96-well plates are prepared. In some embodiments, 2, 3, 4, 5, 7, 8, 9, 10, 11, 12, 13, 14, 15, 16, 17, 18, 19, or 20 plates are prepared.

B) Lysis of the Singles Cells and Extraction of the RNA Molecules,

The step consists in lysing the single cells so as to render the mRNA molecules accessible.

The lysis of the single cells is carried out according to any conventional method known in the art. For instance, said methods comprise contacting the single cells with a lysis mixture under conditions and for a time to produce a lysate and subsequently render the mRNA molecules accessible.

Typically, the lysis mixture comprises a polypeptide having protease activity, a polypeptide having deoxyribonuclease activity, and a surfactant. For instance, the lysis mixture may comprise proteinase K or an enzymatically active mutant or variant thereof, DNase I, and a surfactant comprising TRITON X-114™ at a concentration from 0.02% to 3%, or 0.05% to 2%, or 0.05% to 1%, THESIT™ at a concentration of 0.01% to 5%, or 0.02% to 3%, or 0.05% to 2%, or 0.05% to 1%, or 0.05% to 0.5%, or 0.05% to 0.3%, TRITON X-100™ at a concentration of 0.05% to 3%, or 0.05% to 1%, or 0.05% to 0.3%, NONIDET P-40™ at a concentration of 0.05% to 5%, or 0.1% to 3%, or 0.1% to 2%, or 0.1% to 1% or 0.1% to 0.3% or 0.1% to 5%, or a combination thereof, and wherein the lysis mixture is substantially free of a cation chelator.

Most importantly, the lysis mixture comprise an RNase inhibitor so as to preserve integrity of RNA molecules. As used herein, the term "RNAse inhibitor" refers to a protein, protein fragment, peptide or small molecule which inhibits the activity of any or all of the known RNAses, including RNase A, RNase B, RNase C, RNase T1, RNase H, RNase P, RNAse I and RNAse III. Some examples of known, but non-limiting, RNAse inhibitors include SCRIPTGUARD (an RNAse inhibitor available from Epicentre Biotechnologies, of Madison, Wis.), SUPERASE-IN (an RNAse inhibitor available from AMBION of Austin, Tex.), Stop RNase Inhibitor STOP RNASE INHIBITOR (an RNASe inhibitor available from 5 PRIME Inc., of Gaithersburg, Md.), ANTI-RNase (AMBION), RNase Inhibitor (Cloned) (AMBION), RNASEOUT (RNaseOUT™) (an RNASe inhibitor available from INVITROGEN of Carlsbad, Calif.), Ribonuclease Inhib III (an RNASe inhibitor available from INVITROGEN), RNASIN (RNasin®) (an RNASe inhibitor available from PROMEGA of Madison, Wis.), PROTECTOR RNase Inhibitor (an RNASe inhibitor available from Roche Applied Science, of Indianapolis, Ind.), Placental RNase Inhibitor (an RNASe inhibitor available from USB, of Cleveland, Ohio) and PROTECTRNA (ProtectRNA™) (an RNASe inhibitor available from SIGMA of St Louis, Mo.). In some embodiments, an RNase inhibitor may be added to the location of the cell, for example, a well containing the cell or cells to be analyzed, at a concentration sufficient to significantly inhibit RNAse activity in the well, by 1-100%, preferably 20-100%, most preferably 50-100%. Preferably the lysis mixture is compatible with in situ reverse transcriptase and DNA polymerase reactions.

In some embodiments, the lysis mixture can be further combined with reagents for reverse transcription as performed in the next step.

In particular, the lysis mixture typically comprises an amount of dNTP. As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescence label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine.

In some further embodiments, the lysis mixture comprises an amount of a primer (i.e. "Oligo-dT RT primer") suitable for priming the reverse transcription of polyadenylated mRNAs while incorporating a universal PCR handle at the 3'-end of cDNA molecules. Typically, said primers consists of the sequence TGCGGTATCTAAAGCGGTGAGTTTTTTTTTTTTTTTTTTTTTTTTTTTTTTVN (SEQ ID NO: 195) wherein V represents either dG, dA, or dC) and then by N represents dA, dT, dG, or dC).

C) Reverse Transcription (RT) of Said RNA Molecules:

The step consist of the reverse transcription (RT) of the RNA molecules extracted at the preceding step or comprising in the RNA samples. According to the present invention, the step uses 96 different well-specific template switching oligonucleotides (TSO) to introduce a well-specific DNA barcode in the 5'-end of cDNAs. Said different well-specific template switching oligonucleotides are sequences SEQ ID NO:99-194. Accordingly the cDNA for a specific well will be identified by the read of the specific barcode.

D) Amplification of the cDNA Obtained at Step C):

The steps consists of an amplification reaction of the cDNAs produced at the preceding step.

As used herein, an "amplification reaction" refers to the reaction mixture in which the amplification of a nucleotide sequence can occur thereby increasing the number of copies of the nucleic acid sequence by enzymatic means. Amplification procedures are well-known in the art and typically includes polymerase chain reaction (PCR). Typically, amplification is carried out with a pair of bi-directional primers (i.e., a primer pair) consisting of one forward and one reverse primer or provided as a pair of forward primers as commonly used in the art of DNA amplification such as in PCR amplification. As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of a primer can depend on many factors, including, but not limited to temperature and composition (A/T vs. G/C content) of the primer. Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

According to the present invention, the PCR-based amplification uses the PCR handle incorporated 5' in the TSO. Thus, in some embodiments, the PCR reaction is carried out with a forward primer that is complementary to the PCR handle sequence of the TSO and a reverse primer which hybridizes to the 3'-end PCR handle which was incorporated through the Oligo-dT RT primer. In some embodiments, the PCR-based amplification uses a pair of primers said that consists of the sequence AGACGTGTGCTCTTCCGATCT (SEQ ID NO:196) for the forward primer and the sequence TGCGGTATCTAAAGCGGTGAG (SEQ ID NO:197) for the reverse primer.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). Molecular Cloning: A Laboratory Manual, Third Edition, Cold Spring Harbor Laboratory Press, Cold Spring Harbor, N.Y., United States of America. Generally, lower salt concentration and higher temperature hybridization and/or washes increase the stringency of hybridization conditions. Typically, amplification is carried out with a thermal cycler. In some embodiments, the amplification is carried out by incubating at 98° C. for 3 min, followed by 22 cycles of (98° C. for 15 sec, 67° C. for 20 sec, 72° C. for 6 min).

E) cDNA Pooling and Purification:

The step consists in pooling the amplified cDNA of each well into a single container (e.g. tube) and then to purify it to remove primers and reagents from PCRs. Typically, purification involves use of magnetic beads or particles functionalized with silica surfaces to allow selective binding of DNA in the presence of high concentrations of salt. DNA bound to a magnetic bead can be easily separated from the aqueous phase using a magnet; thereby allowing rapid sample processing and fine control of solution volumes.

F) Preparation of a cDNA Library:

The step consists of subjecting the cDNAs purified at the preceding step to a tagmentation reaction.

As used herein, the term "tagmentation reaction" refers to incubation of the cDNA with transposomes or transposition complexes to tag and fragment said cDNA with transposon ends. As used herein, the term "transposase" or "fragmentation and labeling enzyme" refers to an enzyme, which is a component of a functional nucleic acid-protein complex capable of transposition and which is mediating transposition. As used herein, the term "transposon end" or "transposon end sequence" refers to a double stranded DNA that exhibits nucleotide sequences that are necessary to form the complex with the transposase enzyme that is functional in an in vitro transposition reaction. The transposon end sequences are responsible for identifying the transposon for transposition. A transposon end forms a transposome or transposition complex with a transposase to perform transposition reaction. In some embodiments, the transposon end sequence may further include additional sequences such as primer binding sites or other functional sequences.

In some embodiments, tagmentation is carried out with NEXTERA (Nextera™) DNA sample preparation kits (DNA sample preparation kits available from Illumina, Inc.) wherein genomic DNA can be fragmented by an engineered transposome that simultaneously fragments and tags input DNA ("tagmentation") thereby creating a population of fragmented nucleic acid molecules which comprise unique adapter sequences at the ends of the fragments.

Typically, tagmentation involves use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and $R^2$ end sequences (Mizuuchi, K., Cell, 35:785, 1983; Savilahti, H, et al., EMBO J., 14:4893, 1995). An exemplary transposase recognition site that forms a complex with a hyperactive Tn5 transposase (e.g., EZ-TN5 (EZ-Tn5™) Transposase, a transposase recognition site available from Epicentre Biotechnologies, of Madison, Wis.). More examples of transposition systems that can be used include *Staphylococcus aureus* Tn552 (Colegio et al., J. Bacteriol., 183:2384-8, 2001; Kirby C et al., Mol. Microbiol., 43:173-86, 2002), Ty1 (Devine & Boeke, Nucleic Acids Res., 22:3765-72, 1994 and International Publication WO 95/23875), Transposon Tn7 (Craig, N L, Science. 271:1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15:5470-9, 1996), Tc1 (Plasterk R H, Curr. Topics Microbiol. Immunol., 204:125-43, 1996), P Element (Gloor, G B, Methods Mol. Biol., 260:97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204:1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include IS5, Tn10, Tn903, IS911, and engineered versions of transposase family enzymes (Zhang et al., (2009) PLOS Genet. 5: e1000689. Epub 2009 Oct. 16; Wilson C. et al (2007) J. Microbiol. Methods 71:332-5).

As used herein, the term "adapter" refers to a non-target nucleic acid component, generally DNA, which is joined to a target polynucleotide fragment and serves a function in subsequent analysis of the target polynucleotide fragment. In some embodiments, an adapter may include a nucleotide sequence that permits identification, recognition, and/or molecular or biochemical manipulation of the polynucleotide to which the adapter is attached. For example, an adapter may include a sequence which may be used as a primer binding site to read the sequence of the polynucleotide fragments. In another example, an adapter may include a barcode sequence which allows barcoded polynucleotide fragments to be identified. In some embodiments, the barcode is selected from the group consisting of:

| i7 barcode | SEQ ID NO: |
|---|---|
| CTACCAGG | 198 |
| CATGCTTA | 199 |
| GCACATCT | 200 |
| TGCTCGAC | 201 |
| AGCAATTC | 202 |
| AGTTGCTT | 203 |
| CCAGTTAG | 204 |
| TTGAGCCT | 205 |
| ACCAACTG | 206 |
| GGTCCAGA | 207 |
| GTATAACA | 208 |
| TTCGCTGA | 209 |
| AACTTGAC | 210 |
| CACATCCT | 211 |
| TCGGAATG | 212 |
| AAGGATGT | 213 |

In some embodiments, an adapter consists of the sequence CAAGCAGAAGACGGCAT-ACGAGATXXXXXXXXGTGACTGGAGTTCA-GACGTGTG CTCTTCCGATCT wherein XXXXXXXX represents the barcode sequence.

In some embodiments, the tagmentation is performed with the plurality of sequences of SEQ ID NO:214 to SEQ ID NO:229.

| Primer name | Custom i7 primer (5' → 3') PM | SEQ ID NO: |
|---|---|---|
| i7_BC1_PM | CAAGCAGAAGACGGCATACGAGATCCTGGT AGGTGACTGGAGTTCAGACGTGTGCTCTTC CGATCT | 214 |
| i7_BC2_PM | CAAGCAGAAGACGGCATACGAGATTAAGCA TGGTGACTGGAGTTCAGACGTGTGCTCTTC CGATCT | 215 |
| i7_BC3_PM | CAAGCAGAAGACGGCATACGAGATAGATGT GCGTGACTGGAGTTCAGACGTGTGCTCTTC CGATCT | 216 |
| i7_BC4_PM | CAAGCAGAAGACGGCATACGAGATGTCGAG CAGTGACTGGAGTTCAGACGTGTGCTCTTC CGATCT | 217 |
| i7_BC5_PM | CAAGCAGAAGACGGCATACGAGATGAATTG CTGTGACTGGAGTTCAGACGTGTGCTCTTC CGATCT | 218 |
| i7_BC6_PM | CAAGCAGAAGACGGCATACGAGATAAGCAA CTGTGACTGGAGTTCAGACGTGTGCTCTTC CGATCT | 219 |
| i7_BC7_PM | CAAGCAGAAGACGGCATACGAGATCTAACT GGGTGACTGGAGTTCAGACGTGTGCTCTTC CGATCT | 220 |
| i7_BC8_PM | CAAGCAGAAGACGGCATACGAGATAGGCTC AAGTGACTGGAGTTCAGACGTGTGCTCTTC CGATCT | 221 |
| i7_BC9_PM | CAAGCAGAAGACGGCATACGAGATCAGTTG GTGTGACTGGAGTTCAGACGTGTGCTCTTC CGATCT | 222 |
| i7_BC10_PM | CAAGCAGAAGACGGCATACGAGATTCTGGA CCGTGACTGGAGTTCAGACGTGTGCTCTTC CGATCT | 223 |
| i7_BC11_PM | CAAGCAGAAGACGGCATACGAGATTGTTAT ACGTGACTGGAGTTCAGACGTGTGCTCTTC CGATCT | 224 |
| i7_BC12_PM | CAAGCAGAAGACGGCATACGAGATTCAGCG AAGTGACTGGAGTTCAGACGTGTGCTCTTC CGATCT | 225 |
| i7_BC13_PM | CAAGCAGAAGACGGCATACGAGATGTCAAG TTGTGACTGGAGTTCAGACGTGTGCTCTTC CGATCT | 226 |
| i7_BC14_PM | CAAGCAGAAGACGGCATACGAGATAGGATG TGGTGACTGGAGTTCAGACGTGTGCTCTTC CGATCT | 227 |
| i7_BC15_PM | CAAGCAGAAGACGGCATACGAGATCATTCC GAGTGACTGGAGTTCAGACGTGTGCTCTTC CGATCT | 228 |
| i7_BC16_PM | CAAGCAGAAGACGGCATACGAGATACATCC TTGTGACTGGAGTTCAGACGTGTGCTCTTC CGATCT | 229 |

Finally, the library of barcoded polynucleotide fragments is purified by typically the same technique as described for the preceding step, i.e. by using the magnetic beads that will remove the reagents (e.g. adapters). In some embodiments, the library can then be further characterized before sequencing in the following step. For example, the distribution of fragment sizes of the fragments can be measured using a Bioanalyzer, Fragment Analyzer, or by integrating the signal intensity along an agarose gel. The resulting library is expected to have a broad size distribution (300-1000 b.p.) with an average size of 600-800 b.p.

G) Sequencing the cDNA Library:

The step consists of sequencing the cDNA library as prepared according to the preceding step.

As used herein, the term "sequencing" generally means a process for determining the order of nucleotides in a nucleic acid. A variety of methods for sequencing nucleic acids is well known in the art and can be used.

In some embodiments, next generation sequencing is carried out. As used herein, the term "next generation sequencing" has its general meaning in the art and refers to sequencing technologies having increased throughput as compared to traditional Sanger- and capillary electrophoresis-based approaches, for example with the ability to generate hundreds of thousands or millions of relatively short sequence reads at a time. Some examples of next generation sequencing techniques include, but are not limited to, sequencing by synthesis, sequencing by ligation, and sequencing by hybridization. Accordingly, the sequencing is carried out with a sequencer. In some embodiments, the sequencer is configured to perform next generation sequencing (NGS). In some embodiments, the sequencer is configured to perform massively parallel sequencing using sequencing-by-synthesis with reversible dye terminators. In some embodiments, the sequencer is configured to perform sequencing-by-ligation. In yet other embodiments, the sequencer is configured to perform single molecule sequencing. A next-generation sequencer can include a number of different sequencers based on different technologies, such as ILLUMINA (SOLEXA) sequencing, ROCHE 454 sequencing, ION TORRENT sequencing, SOLID (SOLID™) sequencing, and the like. An example of a sequencing technology that can be used in the present methods is the Illumina platform. The Illumina platform is based on amplification of DNA on a solid surface (e.g., flow cell) using fold-back PCR and anchored primers (e.g., capture oligonucleotides). For sequencing with the Illumina platform, DNA is thus fragmented, and adapters are added to both terminal ends of the fragments (see the preceding step). DNA fragments are attached to the surface of flow cell channels by capturing oligonucleotides which are capable of hybridizing to the adapter ends of the fragments. The DNA fragments are then extended and bridge amplified. After multiple cycles of solid-phase amplification followed by denaturation, an array of millions of spatially immobilized nucleic acid clusters or colonies of single-stranded nucleic acids are generated. Each cluster may include approximately hundreds to a thousand copies of single-stranded DNA molecules of the same template. The Illumina platform uses a sequencing-by-synthesis method where sequencing nucleotides comprising detectable labels (e.g., fluorophores) are added successively to a free 3' hydroxyl group. After nucleotide incorporation, a laser light of a wavelength specific for the labeled nucleotides can be used to excite the labels. An image is captured and the identity of the nucleotide base is recorded. These steps can be repeated to sequence the rest of the bases. Sequencing according to this technology is described in, for example, U.S. Patent Publication Application Nos. 2011/0009278, 2007/0014362, 2006/0024681, 2006/0292611, and U.S. Pat. Nos. 7,960,120, 7,835,871, 7,232,656, and 7,115,200, each of which is incorporated herein by reference in its entirety.

According to the present invention a plurality of reads will be obtained. As used herein, the term "read" refers to a sequence read from a portion of a nucleic acid sample. Typically, a read represents a short sequence of contiguous base pairs in the sample. The read may be represented symbolically by the base pair sequence in A, T, C, and G of the sample portion, together with a probabilistic estimate of the correctness of the base (quality score).

In some embodiments, the reads are obtained with the following primers:

| Name | Sequence | SEQ ID NO: |
|---|---|---|
| Custom Illumina Read 1 sequencing primer | TCGTCGGCAGCGTCAGA TGTGTATAAGAGACAG | 230 |
| Custom Illumina i7 sequencing primer | AGATCGGAAGAGCACAC GTCTGAACTCCAGTCAC | 231 |
| Custom Illumina Read 2 sequencing primer | GTGACTGGAGTTCAGAC GTGTGCTCTTCCGATCT | 232 |

According to the present invention, 3 reads are obtained for which 4 categories of information can be obtained:

Read1 allows identifying the gene from which the mRNA was transcribed.

Read i7 allows identifying the plate by detecting the specific i7 barcodes of the adapter, and thus will allow identifying the specific plate. In other words, the reads inform the analyzer of the data that these barcodes should be treated as a single barcode group corresponding to plate.

Read 2 allows identifying the well by detecting the specific barcode sequence specific for the well, said information will thus associate the detection and quantification the individual sequences to a specific well and subsequently to a specific single cell. In other words, the reads inform the analyzer of the data that these barcodes should be treated as a single barcode group corresponding to a specific well (i.e. a single cell).

Read 2 also allows identifying and quantifying the individual molecules present in the library by detecting the UMI sequences.

Thus by aligning and mapping the specific sequence to a specific gene, the method will thus allow detecting the expression of said specific gene as well as quantification of said expression level. Alignment is typically implemented by a computer algorithm. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. patent application Ser. No. 14/354,528, filed Apr. 25, 2014, which is incorporated herein by reference in its entirety. The matching of a sequence read in aligning can be a 100% sequence match or less than 100% (i.e., a non-perfect match).

Accordingly the combination of the reads allow the detection and quantification of expression of a plurality of genes in a single cell. Typically, analysis of the different reads including pooling the information by plates and wells may be performed by a bioinformatic algorithm.

Applications:

The RNA sequencing (RNAseq) method of the present invention may find various applications and is particularly suitable for the cost effective integrative analysis of B and T cell transcriptome and paired BCR and TCR repertoire in phenotypically defined B and T cell subsets of a subject.

The single-cell RNA sequencing (scRNAseq) method of the present invention may find various applications and is particularly suitable for the cost effective integrative analysis of B and T cell transcriptome and paired BCR and TCR repertoire in phenotypically defined B and T cell subsets of a subject.

The subject is preferably a human subject but can also be derived from non-human subjects, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits.

Accordingly, the RNA sample and/or single cells are prepared from a sample obtained from a subject. As used herein, "sample" includes, but is not limited to, components derived from a subject (body fluid such as blood or the like). In some embodiments, the sample is a body fluid sample or a tissue sample. In some embodiments, the sample is selected from the group consisting of blood, plasma, serum, bone marrow, semen, vaginal secretions, urine, amniotic fluid, cerebrospinal fluid, synovial fluid and biopsy tissue samples, including from infection and/or tumor locations. The sample can be a tumor biopsy. The biopsy can be from, for example, from a tumor of the brain, liver, lung, heart, colon, kidney, or bone marrow. Typically, the tissue sample is enzymatically disaggregated with collagenase and DNase I to obtain a suspension of cells.

As used herein, the term "B cell receptor" or "BCR" refers to the antigen receptor at the plasma membrane of B cells. A BCR is known as an immunoglobulin (Ig). A membrane-bound Ig acts as an antigen receptor molecule as a BCR. A secretory protein thereof is secreted to the outside of a cell as an antibody. A large amount of antibodies is secreted from a terminally differentiated plasma cell and has functions to eliminate pathogens by binding to a pathogenic molecule such as a virus or bacteria or by a subsequent immune reaction such as a complement binding reaction. A BCR is expressed on a B cell surface. After binding to an antigen, the BCR transmits an intracellular signal to initiate various immune responses or cell proliferation. Diversity of amino acid sequences at an antigen-binding site is responsible for the specificity of a BCR. Sequences at an antigen-binding site greatly vary among BCR molecules and are called variable sections (V regions). Meanwhile, a sequence of a constant region (C region) is highly conserved among BCR molecules or antibody molecules. Such a region has an effector function of an antibody or a signaling function of a receptor. A BCR and an antibody are the same except for the presence or absence of a membrane-binding domain. An Ig molecule consists of polypeptide chains, two heavy chains (H chains) and two light chains (L chains). In one Ig molecule, two H chains, or one H chain and one L chain, are bound by a disulfide bond. There are 5 different H chain classes (isotypes) called μ chain, α chain, γ chain, δ chain, and ε chain in Ig, which are called IgM, IgA, IgG, IgD, and IgE, respectively. It is known that functions and roles generally vary depending on the isotype, e.g., an antibody with a high level of specificity which is functional in biological defense is an IgG antibody, an IgA antibody is involved in mucosal immunity, and an IgE antibody is important in allergy, asthma, and atopic dermatitis. Furthermore, it is known that there are several types of subclasses in isotypes, such as IgG1, IgG2, IgG3, and IgG4. It is understood that there are two types of L chains, 2 chain (IgL) and κ chain (IgK), which can bind to an H chain of any class, and there is no functional difference there between. BCR genes are formed by gene rearrangement that occurs in a somatic cell. A variable section is encoded in a few separate gene fragments in the genome, which induce somatic cell genetic recombination in the differentiation process of a cell. A genetic sequence of a variable section of an H chain consists of a C region (constant region, C) defining an isotype that is different from a D region, a J region, and a V region. Each gene fragment is separated in the genome, but is expressed as a series of V-D-J-C genes by gene rearrangement. The database of the IMGT has 38-44 types of functional IgH chain V gene fragments (IGHV), 23 types of D gene fragments (IGHD), 6 types of J gene fragments (IGHJ), 34 types of functional IgK chain V gene fragments (IGKV), 5 types of J gene fragments (IGKJ), 29-30 types of functional IgL chain V gene fragments (IGLV), and 5 types of J gene fragments (IGLJ). These gene fragments undergo gene rearrangement to ensure diversity of BCRs. Furthermore, highly diverse CDR3 regions are formed by a random insertion or deletion in an amino acid sequence as in TCRs.

As used herein, the term "TCR" has its general meaning in the art and refers to the molecule found on the surface of T cells that is responsible for recognizing antigens bound to MHC molecules. During antigen processing, antigens are degraded inside cells and then carried to the cell surface in the form of peptides bound to major histocompatability complex (MHC) molecules (human leukocyte antigen HLA molecules in humans). T cells are able to recognize these peptide-MHC complex at the surface of professional antigen presenting cells or target tissue cells such as β cells in TID. There are two different classes of MHC molecules: MHC Class I and MHC Class II that deliver peptides from different cellular compartments to the cell surface that are recognized by CD8+ and CD4+ T cells, respectively. The T cell receptor or TCR is the molecule found on the surface of T cells that is responsible for recognizing antigens bound to MHC molecules. The TCR heterodimer consists of an alpha and beta chain in 95% of T cells, whereas 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. Each chain of the TCR is a member of the immunoglobulin superfamily and possesses one N-terminal immunoglobulin (Ig)-variable (V) domain, one Ig-constant (C) domain, a transmembrane region, and a short cytoplasmic tail at the C-terminal end. The constant domain of the TCR consists of short connecting sequences in which a cysteine residue forms a disulfide bond, making a link between the two chains. The structure allows the TCR to associate with other molecules like CD3 which possess three distinct chains (γ, δ, and ε) in mammals and the ξ-chain. These accessory molecules have negatively charged transmembrane regions and are vital to propagating the signal from the TCR into the cell. The CD3 chains, together with the TCR, form what is known as the TCR complex. The signal from the TCR complex is enhanced by simultaneous binding of the MHC molecules by a specific co-receptor. On helper T cells, this co-receptor is CD4 (specific for class II MHC); whereas on cytotoxic T cells, this co-receptor is CD8 (specific for class I MHC). The co-receptor not only ensures the specificity of the TCR for an antigen, but also allows prolonged engagement between the antigen presenting cell and the T cell and recruits essential molecules (e.g., LCK) inside the cell involved in the signaling of the activated T lymphocyte. The term "T-cell receptor" is thus used in the conventional sense to mean a molecule capable of recognising a peptide when presented by an MHC molecule. The molecule may be a heterodimer of two chains α and β (or optionally γ and δ) or it may be a recombinant single chain TCR construct. The variable domain of both the TCR α-chain and β-chain have three hypervariable or complementarity determining regions (CDRs). CDR3 is the main CDR responsible for recognizing processed antigen. Its hypervariability is determined by recombination events that bring together segments from different gene loci carrying several possible alleles. The genes involved are V and J for the TCR α-chain and V, D and J for the TCR β-chain. Further amplifying the diversity of this CDR3 domain, random nucleotide deletions and additions during recombination take place at the junction of V-J for TCR α-chain, thus giving rise to V(N)J sequences; and V-D and D-J for TCR β-chain, thus giving rise to V(N)D(N)J sequences. Thus, the number of possible CDR3 sequences generated is immense and accounts for the wide capability of the whole TCR repertoire to recognize a number of disparate antigens. At the same time, this CDR3 sequence constitutes a specific molecular fingerprint for its corresponding T cell. Rearranged nucleotide sequences are presented as V segments (underlined) followed by (ND) N segments (not underlined; N additions denoted in bold) and then by J segments (underlined), as annotated using the IMGT database (imgt.org).

In some embodiments, the RNA seq and/or scRNAseq method of the present invention is particularly suitable for obtaining a dataset that includes sequence information, representation of V, D, J, C, VJ, VDJ, VJC, VDJC, antibody heavy chain, antibody light chain, CDR3, or T-cell receptor usage, representation for abundance of V, D, J, C, VJ, VDJ, VJC, VDJC, antibody heavy chain, antibody light chain, CDR3, or T-cell receptor and unique sequences; representation of mutation frequency, correlative measures of VJ V, D, J, C, VJ, VDJ, VJC, VDJC, antibody heavy chain, antibody light chain, CDR3, or T-cell receptor usage, etc. Such results may then be output or stored, e.g. in a database of repertoire analyses, and may be used in comparisons with test results, reference results, and the like.

After obtaining an immune repertoire analysis result from the sample being assayed, the repertoire can be compared with a reference or control repertoire to make the desired analysis. Determination or analysis of the difference between two repertoires can be performed using any conventional methodology, where a variety of methodologies are known to those of skill in the array art, e.g., by comparing databases of usage data, etc. A statistical analysis step can then be performed to obtain the weighted contribution of the sequence prevalence, e.g. V, D, J, C, VJ, VDJ, VJC, VDJC, antibody heavy chain, antibody light chain, CDR3, or T-cell receptor usage, mutation analysis, etc. A statistical analysis may comprise use of a statistical metric (e.g., an entropy metric, an ecology metric, a variation of abundance metric, a species richness metric, or a species heterogeneity metric.) in order to characterize diversity of a set of immunological receptors. A statistical metric may also be used to characterize variation of abundance or heterogeneity.

In some embodiments, the RNAseq and/or scRNAseq method of the present invention is particularly suitable for determining the presence and frequency of a clonotype. As used herein, the term “clonotype” means a rearranged or recombined nucleotide sequence of a lymphocyte which encodes an immune receptor or a portion thereof. More particularly, clonotype means a recombined nucleotide sequence of a T cell or B cell which encodes a T cell receptor (TCR) or B cell receptor (BCR), or a portion thereof. In various embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, a VD rearrangement of TCR δ, a Kde-V rearrangement, or the like. Clonotypes may also encode translocation breakpoint regions involving immune receptor genes. In one aspect, clonotypes have sequences that are sufficiently long to represent or reflect the diversity of the immune molecules that they are derived from.

Thus in some embodiments, the RNAseq and/or scRNAseq method of the present invention allows detection of the repertoire of rearranged T-cell or B-cell receptors, partially or fully. In particular, analysis of a TCR or BCR repertoire is a useful analytical tool for analysing monoclonality or immune disorder. The RNAseq and/or scRNAseq method of the present invention may thus be used or applied for the diagnosis of an immune response in the subject. In particular, the repertoire of T- and B-cells will change in response to stimulation of the immune system upon exposure to various external and internal stimuli, ranging from allergens, toxins, autoantigen to pathogens. The results of the VDJ rearrangement, nucleotide deletion and insertion, and hypermutation pathway in response to these stimuli can now be visualized in a convenient way by carrying out the RNAseq and/or scRNAseq method of the present invention. The RNAseq and/or scRNAseq method of the present invention allows detection of both predominant rearrangements that are induced in response to a certain agent. Once a pattern of rearrangements has been established, T- and/or B-cell repertoires of subjects may be diagnosed using the RNAseq and/or scRNAseq method of the present invention to detect an immune response, which immune response may be associated with clinical symptoms or a disease. In some embodiments, the RNAseq and/or scRNAseq method of the present invention allows both identification and monitoring of T cell clones without a priori knowledge of variable sequence, antigen specificity, or T cell phenotype. The method has sufficient resolution to detect single clones and sufficient sensitivity to pick up expansion of T cell clones early after antigenic exposure or stimulation or infection. In some embodiments, the RNAseq and/or scRNAseq method of the present invention can be used for rapid, complete, unbiased screening of the B- and T cell repertoire for the presence of dominant clones or changes in the BCR or TCR repertoire or composition. After identifying the clone-specific sequences using the described method, full nucleotide sequences of dominant BCR or TCR chains can be obtained. The resulting information regarding repertoire constellation, repertoire changes and dominant clones will find applications in diagnostics and medicine.

Thus, the RNAseq and/or scRNAseq method of the present invention is thus advantageous for use in the diagnosis of infectious diseases, autoimmune disease, and cancer.

In some embodiments, the RNAseq and/or scRNAseq method of the present invention finds application in diagnosis of an autoimmune inflammatory disease. In some embodiments, the autoimmune inflammatory disease is selected from the group consisting of arthritis, rheumatoid arthritis, acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma, systemic scleroderma, sclerosis, systemic sclerosis, multiple sclerosis (MS), spino-optical MS, primary progressive MS (PPMS), relapsing remitting MS (RRMS), progressive systemic sclerosis, atherosclerosis, arteriosclerosis, sclerosis disseminata, and ataxic sclerosis, inflammatory bowel disease (IBD), Crohn's disease, colitis, ulcerative colitis, colitis ulcerosa, microscopic colitis, collagenous colitis, colitis polyposa, necrotizing enterocolitis, transmural colitis, autoimmune inflammatory bowel disease, pyoderma gangrenosum, erythema nodosum, primary sclerosing cholangitis, episcleritis, respiratory distress syndrome, adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis, Rasmussen's encephalitis, limbic and/or brainstem encephalitis, uveitis, anterior uveitis, acute anterior uveitis, granulomatous uveitis, nongranulomatous uveitis, phacoantigenic uveitis, posterior uveitis, autoimmune uveitis, glomerulonephritis (GN), idiopathic membranous GN or idiopathic membranous nephropathy, membrano- or membranous proliferative GN (MPGN), rapidly progressive GN, allergic conditions, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis, lymphomatoid granulomatosis, Wegener's granulomatosis, agranulocytosis, vasculitides, including vasculitis, large vessel vasculitis, polymyalgia rheumatica, giant cell (Takayasu's) arteritis, medium vessel vasculitis, Kawasaki's disease, polyarteritis nodosa, microscopic polyarteritis, CNS vasculitis, necrotizing, cutaneous, hypersensitivity vasculitis, systemic necrotizing vasculitis, and ANCA-associated vasculitis, such as Churg-Strauss vasculitis or syndrome (CSS), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus, optionally pemphigus vulgaris, pemphigus foliaceus, pemphigus mucus-membrane pemphigoid, pemphigus erythematosus, autoimmune polyendocrinopathies, Reiter's disease or syndrome, immune complex nephritis, antibody-mediated nephritis, neuromyelitis optica, polyneuropathies, chronic neuropathy, IgM polyneuropathies, IgM-mediated neuropathy, thrombocytopenia, thrombotic thrombocytopeni purpura (TTP), idiopathic thrombocytopenia purpura (ITP), autoimmune orchitis and oophoritis, primary hypothyroidism, hypoparathyroidism, autoimmune thyroiditis, Hashimoto's disease, chronic thyroiditis (Hashimoto's thyroiditis); subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis, allergic encephalomyelitis, experimental allergic encephalomyelitis (EAE), myasthenia gravis, thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AGED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis, optionally benign monoclonal gammopathy or monoclonal garnmopathy of undetermined significance, MGUS, peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired splenic atrophy, infertility due to antispermatozoan antobodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Lofller's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In some embodiments, the RNAseq and/or scRNAseq method of the present invention is particularly suitable for diagnosing an infectious disease. As used herein the term "infectious disease" includes any infection caused by viruses, bacteria, protozoa, molds or fungi. In some embodiments, the viral infection comprises infection by one or more viruses selected from the group consisting of *Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, Tymoviridae, Hepadnaviridae, Herpesviridae, Paramyxoviridae or Papillomaviridae viruses. Relevant taxonomic families of RNA viruses include, without limitation, Astroviridae, Birnaviridae, Bromoviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae*, and *Tymoviridae* viruses. In some embodiments, the viral infection comprises infection by one or more viruses selected from the group consisting of adenovirus, rhinovirus, hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe, pachindae viruses, adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viruses, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, and Kyasanur forest disease. Bacterial infections that can be treated according to this invention include, but are not limited to, infections caused by the following: *Staphylococcus; Streptococcus*, including *S. pyogenes; Enterococcl; Bacillus*, including *Bacillus anthracis*, and *Lactobacillus; Listeria; Corynebacterium diphtheriae; Gardnerella* including *G.*

*vaginalis; Nocardia; Streptomyces; Thermoactinomyces vulgaris; Treponerna; Camplyobacter, Pseudomonas* including *aeruginosa; Legionella; Neisseria* including *N. gonorrhoeae* and *N. meningitides; Flavobacterium* including *F. meningosepticum* and *F. odoraturn; Brucella; Bordetella* including *B. pertussis* and *B. bronchiseptica; Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus; Rickettsiaceae* including *R. fickettsfi, Chlamydia* including *C. psittaci* and *C. trachornatis; Mycobacterium* including *M. tuberculosis, M. intracellulare, M. folluiturn, M. laprae, M. avium, M. bovis, M. africanum, M. kansasii, M. intracellulare*, and *M. lepraernurium*; and *Nocardia*. Protozoa infections that may be treated according to this invention include, but are not limited to, infections caused by leishmania, kokzidioa, and trypanosoma. A complete list of infectious diseases can be found on the website of the National Center for Infectious Disease (NCID) at the Center for Disease Control (CDC) (World Wide Web (www) at cdc.gov/ncidod/diseases/), which list is incorporated herein by reference. All of said diseases are candidates for treatment using the compositions according to the invention.

The RNAseq and/or scRNAseq method of the present invention is also particularly suitable for diagnosing cancer or monitoring cancer progression. It is now well established that characterizing the immune response against the tumor is particularly suitable for predicting survival but also response to some therapies, in particular to immunotherapy performed with immune checkpoint inhibitors (e.g. anti-PD1 antibodies). As used herein, the term "cancer" has its general meaning in the art and includes, but is not limited to, solid tumors and blood-borne tumors. The term cancer includes diseases of the skin, tissues, organs, bone, cartilage, blood and vessels. The term "cancer" further encompasses both primary and metastatic cancers. Examples of cancers that may be treated by methods and compositions of the invention include, but are not limited to, cancer cells from the bladder, blood, bone, bone marrow, brain, breast, colon, esophagus, gastrointestinal tract, gum, head, kidney, liver, lung, nasopharynx, neck, ovary, prostate, skin, stomach, testis, tongue, or uterus. In some embodiments, the subject suffers from a cancer selected from the group consisting of Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant, Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplasia, Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, non-small cell lung cancer (NSCLC) which coexists with chronic obstructive pulmonary disease (COPD), Ocular oncology, Oligoastrocytoma, Oligodendroglioma, Oncocytoma, Optic nerve sheath, meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastema, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute, lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Vemer Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, the RNAseq and/or scRNAseq method of the present invention is particularly suitable for monitoring settlement of an immune response after or during a therapy. Thus the RNAseq and/or scRNAseq method of the present invention may be suitable for optimizing therapy, by analysing the immune repertoire in a sample, and based on that information, selecting the appropriate therapy, dose, treatment modality, etc. that is optimal for stimulating or suppressing a targeted immune response. For example, a patient may be assessed for the immune repertoire relevant to an autoimmune disease, and a systemic or targeted immunosuppressive regimen may be selected based on that information.

In some embodiments, the RNAseq and/or scRNAseq method of the present invention is particularly suitable for assessing a vaccine response. In some embodiments, the RNAseq and/or scRNAseq method of the present invention is suitable for measuring the immunological diversity in response to administration of a vaccine. Accordingly, the sample may be obtained following vaccination, and may further be compared to samples from time points before vaccine administration, or at multiple time points following vaccine administration. For instance, comparing the diversity of the immunological receptors present before and after vaccination, may assist the analysis of the organism's response to the vaccine. The RNAseq and/or scRNAseq method of the present invention may thus be useful in the selection of candidate vaccines; to determine the responsiveness of individuals to candidate vaccines.

In some embodiments, the RNAseq and/or scRNAseq method of the present invention is particularly suitable for assessing clonal rearrangements and/or chromosomal translocations that occur in lymphoma. The term "lymphoma" refers to cancers that originate in the lymphatic system. Lymphoma is characterized by malignant neoplasms of lymphocytes-B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body. Lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

In some embodiments, the RNAseq and/or scRNAseq method of the present invention may also find applications in transplantation. In particular, the RNAseq and/or scRNAseq method of the present invention may be suitable for assessing the immune response that can could lead to transplant rejection. As used herein, the term "transplantation" refers to the process of taking a cell, tissue, or organ, called a "transplant" or "graft" from one subject and placing it or them into a (usually) different subject. The subject who provides the transplant is called the "donor" and the subject who received the transplant is called the "recipient". An organ, or graft, transplanted between two genetically different subjects of the same species is called an "allograft". A graft transplanted between subject s of different species is called a "xenograft". Typically the subject may have been transplanted with a graft selected from the group consisting of heart, kidney, lung, liver, pancreas, pancreatic islets, brain tissue, stomach, large intestine, small intestine, cornea, skin, trachea, bone, bone marrow, muscle, or bladder.

In some embodiments, the RNAseq and/or scRNAseq method of the present invention is particularly suitable for assessing immunosenescence in a subject. As used herein, the term "immunosenescence" refers to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactorial condition leading to many pathologically significant health problems, e.g., in the aged population.

In some embodiments, the RNAseq and/or scRNAseq method of the present invention is particularly suitable for diagnosing immunodeficiencies. For instance, defect in V (D) J recombination can cause severe combined immunodeficiency (i.e, T/B severe combined immunodeficiencies) with a broad spectrum of immune manifestations, such as late-onset combined immunodeficiency and autoimmunity. The earliest molecular diagnosis of these patients is required to adopt the best therapy strategy, particularly when it involves a myeloablative conditioning regimen for hematopoietic stem cell transplantation. The RNAseq and/or scRNAseq method of the present invention fulfills this need.

In some embodiments, the RNAseq and/or scRNAseq method of the present invention can also be applied in fundamental research on T- and B-cell development. Currently, large efforts are invested in order to understand how T- and B-cell develop into various phenotypes. The ability to trace and quantify particular clones is critical in this effort. The method described allows monitoring of the relevant T- and B-cell population in a rapid, sensitive, and in high-resolution.

In some embodiments, the RNAseq and/or scRNAseq method of the present invention may be useful in selection of relevant antibodies, in particular in selection of antibodies that could be used for therapy. In particular, the RNAseq and/or scRNAseq method of the present invention is particularly suitable for determining the clonality of an antibody producing cell. An antibody-producing cell is a cell that produces antibodies. Such cells are typically cells involved in a mammalian immune response (such as a B-lymphocyte and plasma cells) and produce immunoglobulin heavy and light chains that have been "naturally paired" by the immune system of the host. Antibody producing cells include hybridoma cells that express antibodies. An antibody-producing cell may be obtained from an animal which has been immunized with a selected antigen, e.g., a peptide, an animal which has not been immunized with a selected antigen (e.g., an animal having an autoimmune disease) or which has developed an immune response to an antigen as a result of disease or infection. Animals may be immunized with a selected antigen using any of the techniques well known in the art suitable for generating an immune response (see Handbook of Experimental Immunology D. M. Weir (ed.), Vol 4, Blackwell Scientific Publishers, Oxford, England, 1986). Within the context of the present invention, the phrase "selected antigen" includes any substance to which an antibody may be made, including, among others, proteins, carbohydrates, inorganic or organic molecules, transition state analogs that resemble intermediates in an enzymatic process, nucleic acids, cells, including cancer cells, cell extracts, pathogens, including living or attenuated viruses, bacteria, vaccines and the like. As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH). Accordingly, a further object of the present invention relates to a method for selecting an antibody that specifically binds to an antigen of interest comprising (a) immunizing an animal with an antigen of interest; (b) isolating a plurality of B-cells from the immunized animal; (c) characterizing the plurality of B cells by carrying out the RNAseq and/or scRNAseq method of the present invention and (d) providing the sequences of the antibody of interest.

Kits of the Present Invention:

A further object of the present invention relates to a kit or a reagent for practicing one or more of the above-described methods. The subject reagents and kits thereof may vary greatly. For example, reagents can include primer sets for cDNA synthesis, for PCR amplification and/or for high throughput sequencing of a class or subtype of immunological receptors. In particular, the kit of the present invention comprises at least one TSO of the present invention. In some embodiments, the kit of the present invention comprises a plurality of TSO characterized by the presence of different UMI sequences. In some embodiments, the kit of the present invention comprises the 96 TSO as described above. The kits may also include reagents employed in the various methods, such as panel of antibodies for cell sorting, primers, dNTPs, which may be either premixed or separate, one or more uniquely labeled dNTPs, adapter sequences as described above, or other post synthesis labelling reagent, such as chemically active derivatives of fluorescent dyes, enzymes, such as reverse transcriptases, DNA polymerases, RNA polymerases, transposases and the like, various buffer mediums, e.g. hybridization and washing buffers, beads of prufication, and the like. The kits can further include a software package for statistical analysis, and may include a reference database for calculating the probability of a match between two repertoires. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium., on which the information has been recorded. Yet another means that may be present is a website address which may be used via the internet to access the information at a removed, site. Any convenient means may be present in the kits. The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs. Software products (or components) may be tangibly embodied in a machine-readable medium, and comprise instructions operable to cause one or more data processing apparatus to perform operations comprising: a) clustering sequence data from a plurality of immunological receptors or fragments thereof; and b) providing a statistical analysis output on said sequence data. Also provided herein are software products (or components) tangibly embodied in a machine-readable medium, and that comprise instructions operable to cause one or more data processing apparatus to perform operations comprising: storing sequence data for a multitude of sequence reads. In some examples, a software product (or component) includes instructions for assigning the sequence data into V, D, J, C, VJ, VDJ, VJC, VDJC, or VJ/VDJ lineage usage classes or instructions for displaying an analysis output in a multi-dimensional plot. In some cases, a multidimensional plot enumerates all possible values for one of the following: V, D, J, or C. (e.g., a three-dimensional plot that includes one axis that enumerates all possible V values, a second axis that enumerates all possible D values, and a third axis that enumerates all possible J values). In some cases, a software product (or component) includes instructions for identifying one or more unique patterns from a single sample correlated to a condition. The software product (or component) may also include instructions for normalizing for amplification bias. In some examples, the software product (or component) may include instructions for using control data to normalize for sequencing errors or for using a clustering process to reduce sequencing errors. A software product (or component) may also include instructions for using two separate primer sets or a PCR filter to reduce sequencing errors.

The invention will be further illustrated by the following figures and examples. However, these examples and figures should not be interpreted in any way as limiting the scope of the present invention.

FIGURES

FIG. 1: Overview of FB5Pseq experimental workflow. Schematic illustration of the mapping of Read1 sequences on IGH and IGK or IGL amplified cDNA, enabling the in silico reconstruction of paired variable BCR sequences.

Figure 2:
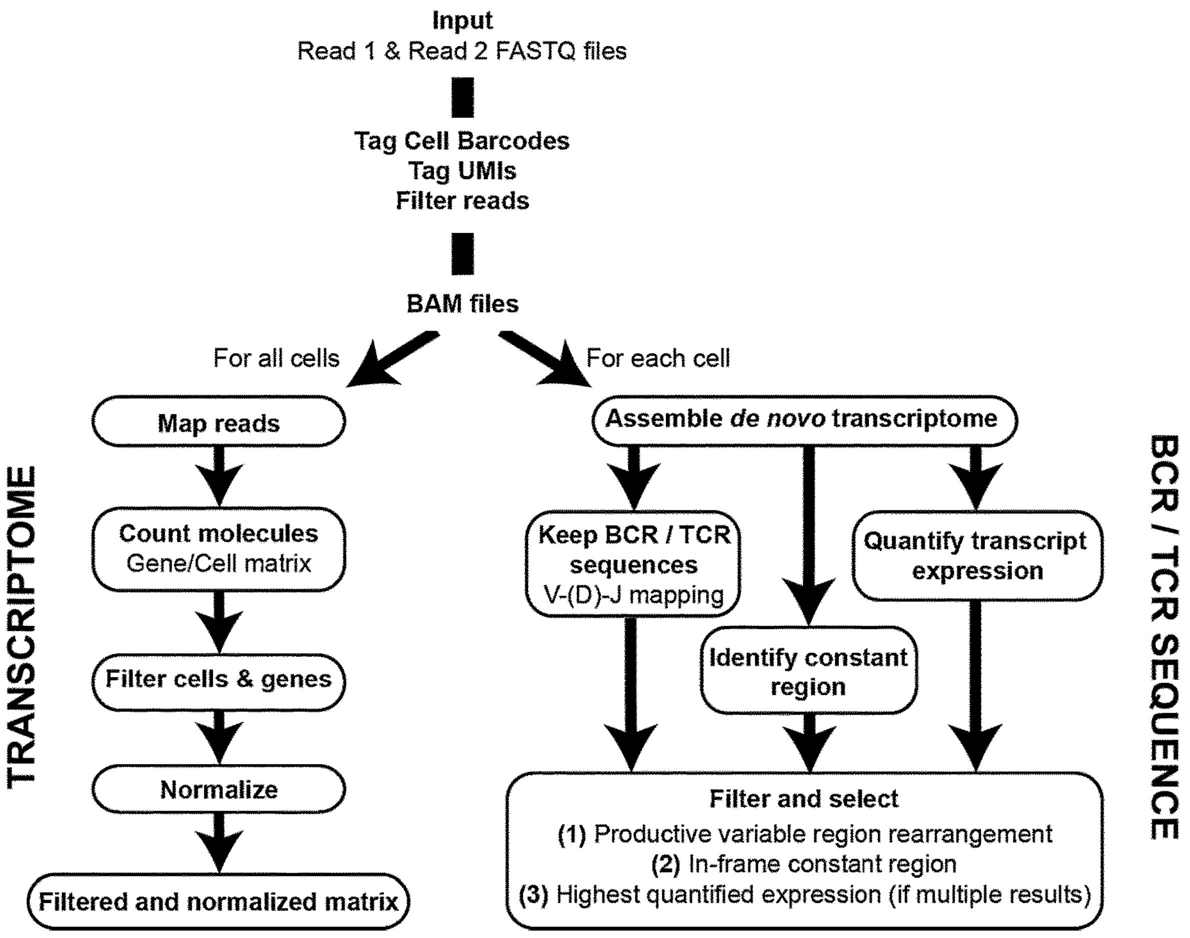

FIG. 2: Overview of FB5Pseq bioinformatics workflow. Major steps of the bioinformatics pipeline starting from Read1 and Read2 FASTQ files for the generation of single-cell gene expression matrices and BCR or TCR repertoire sequences.

FIG. 3: FB5seq quality metrics on human tonsil B cell subsets. (A) Experimental workflow for studying human tonsil B cell subsets with FB5Pseq. (B) Per cell quantitative accuracy of FB5Pseq computed based on ERCC spike-in mRNA detection (see Methods) for Memory B cells (Mem, n=73 Tonsil 1, n=65 Tonsil 2), GC B cells (GC, n=235 Tonsil 1, n=242 Tonsil 2) and PB/PC cells (n=78 Tonsil 1, n=152 Tonsil 2). Black line indicates the median with 95% confidence interval error bars. (C) Molecular sensitivity of FB5Pseq computed on ERCC spike-in mRNA detection rates (see Methods) in two distinct experiments. Dashed lines indicate the number of ERCC molecules required to reach a 50% detection probability. (D-E) Total number of unique genes (D) and molecules (E) detected in human tonsil Mem B cells (n=73 Tonsil 1, n=65 Tonsil 2), GC B cells (n=235 Tonsil 1, n=242 Tonsil 2) and PB/PCs (n=78 Tonsil 1, n=152 Tonsil 2). Black line indicates the median with 95% confidence interval error bars. (F) Pie charts showing the relative proportion of cells with reconstructed productive IGH and IGK/L sequences (1), only IGK/L sequences (2 only IGH sequences (3) or no BCR sequence (white) among Mem B cells, GC B cells and PB/PC cells from Tonsil 1 and Tonsil 2 samples. Total number of cells analyzed for each subset is indicated at the center of the pie chart.

FIG. 4: FB5Pseq analysis of human tonsil B cell subsets. (A) Scatter plots showing IGH mutation frequency in human Tonsil 1 (circles) and Tonsil 2 (triangles) B cells sorted by their IGH isotype and phenotype (Mem B cells: n=11 IgM/IgD+, n=37 IgG+ and n=26 IgA+; GC B cells: n=55 IgM/IgD+, n=174 IgG+ and n=32 IgA+; PB/PC: n=4 IgM/IgD+, n=179 IgG+ and n=42 IgA+PB/PCs. Black line indicates the median. (B) Scatter plots showing IGK/L mutation frequency in human Tonsil 1 (circles) and Tonsil 2 (triangles) B cells sorted by their IGK/L isotype and phenotype (Mem B cells: n=71 Igκ+, n=51 Igλ+; GC B cells: n=253 Igκ+, n=163 Igλ+; PB/PCs: n=139 Igκ+, n=84 Igλ+).

FIG. 5: FB5Pseq analysis of human peripheral blood antigen-specific CD4 T cells. (A) Experimental workflow for studying human peripheral blood *Candida albicans*-specific CD4 T cells with FB5Pseq. (B) Per cell quantitative accuracy of FB5Pseq computed based on ERCC spike-in mRNA detection (see Methods) for *Candida albicans*-specific CD4 T cells (n=82). Black line indicates the median with 95% confidence interval error bars. (C) Total number of unique genes detected in *Candida albicans*-specific CD4 T cells (n=82). Black line indicates the median with 95% confidence interval error bars. (D) Pie charts showing the relative proportion of cells with reconstructed productive TCRA and TCRB sequences (black), only TCRB sequences (3), only TCRA sequences (2) or no TCR sequence (1) among *Candida albicans*-specific CD4 T cells (n=82). (E) Distribution of TCRB clones among *Candida albicans*-specific CD4 T cells (n=67). Black sectors indicate the proportion of TCRB clones (clonotype expressed by ≥2 cells) within single-cells analyzed (white sector: unique clonotypes).

EXAMPLE 1

Material & Methods

Human Samples

Non-malignant tonsil samples from a 35-year old male (Tonsil 1) and a 30-year old female (Tonsil 2) were obtained as frozen live cell suspensions from the CeVi collection of the Institute Carnot/Calym (ANR, France, calym.org/-Viable-cell-collection-CeVi-. html. Peripheral blood mononuclear cells (PBMCs) were collected in Nantes University Hospital and used fresh in peptide restimulation assays for isolating C. alb-specific T cells. Written informed consent was obtained from the donors.

Flow Cytometry and Cell Sorting of B Cell Subsets

Frozen live cell suspensions were thawed at 37° C. in RPMI+10% FCS, then washed and resuspended in FACS buffer (PBS+5% FCS+2 mM EDTA) at a concentration of $10^8$ cells/ml for staining. Cells were first incubated with 2% normal mouse serum and Fc-Block (BD BIOSCIENCES) for 10 min on ice. Then cells were incubated with a mix of fluorophore-conjugated antibodies for 30 min on ice. Cells were washed in PBS, then incubated with the Live/Dead Fixable Aqua Dead Cell Stain (THERMOFISHER) for 10 min on ice. After a final wash in FACS buffer, cells were resuspended in FACS buffer at a concentration of $10^7$ cells/ml for cell sorting on a 4-laser BD FACS Influx (BD Biosciences).

Mem B cells were gated as $CD3^-CD14^-IgD^-CD20^+CD10^-CD38^{lo}CD27^+SSC^{lo}$ single live cells. GC B cells were gated as $CD3^-CD14^-IgD^-CD20^+CD10^+CD38^+$ single live cells. PB/PC cells were gated as $CD3^-CD14^-IgD^-CD38^{hi}CD27^+SSC^{hi}$ single live cells.

Restimulation and Cell Sorting of Antigen-Specific T Cells.

Fresh PBMCs (10-20×$10^6$ cells, final concentration 10×$10^6$ cells/ml) were stimulated for 3 h at 37° C. with 0.6 nmol/ml PepTivator *Candida albicans* MP65 (pool of 15 amino acids length peptides with 11 amino acid overlap, MILTENYI BIOTEC) in RPMI+5% human serum in the presence of 1 μg/ml anti-CD40 (HB14, MILTENYI BIOTEC). After stimulation, PBMCs were labeled with PE-conjugated anti-CD154 (5C8, MILTENYI BIOTEC) and enriched with anti-PE magnetic beads (MILTENYI BIOTEC). After enrichment, cells were stained with PerCP-Cy5.5 anti-CD4 (RPA-T4, BIOLEGEND), ALEXAFLUOR 700 (AF 700) AlexaFluor700 anti-CD3 (SK7, BIOLEGEND) and APC-Cy7 anti-CD45RA (HI100, BIOLEGEND, and antigen-specific T cells were gated as $CD3^+CD4^+$ $CD45RA^-CD154^+$ single live cells for single-cell sorting.

Single-Cell RNAseq

Single cells were FACS sorted into ice-cold 96-well PCR plates (available from THERMOFISHER) containing 2 μl lysis mix per well. The lysis mix contained 0.5 μl 0.4% (v/v) TRITON X-100 (a lysis agent available from SIGMA-ALDRICH), 0.05 μl 40 U/μl RNASEOUT (RnaseOUT™) (an RNASe inhibitor available from THERMOFISHER), 0.08 μl 25 mM dNTP mix (THERMOFISHER), 0.5 μl 10 μM (dT)30_Smarter primer, 0.05 μl 0.5 pg/μl External RNA Controls Consortium (ERCC) spike-ins mix (THERMOFISHER), and 0.82 μl PCR-Grade $H_2O$ (QIAGEN).

For B cell subsets sorting, the index-sorting mode was activated to record the different fluorescence intensity of each sorted single-cell. Index-sorting FCS files were visualized in FlowJo software and compensated parameters values were exported in CSV tables for further processing. For visualization on linear scales in the R programming software, we applied the hyperbolic arcsine transformation on fluorescence parameters. In every 96-well plate, two wells (H1, H12) were left empty and processed throughout the protocol as negative controls.

Immediately after cell sorting, each plate was covered with adhesive film (THERMOFISHER), briefly spun down in a benchtop plate centrifuge, and frozen on dry ice. Plates containing single cells in lysis mix were stored at −80° C. and shipped on dry ice (only T cells) until further processing.

The plate containing single cells in lysis mix was thawed on ice, briefly spun down in a benchtop plate centrifuge, and incubated in a thermal cycler for 3 minutes at 72° C. (lid temperature 72° C.). Immediately after, the plate was placed back on ice and 3 μl RT mastermix was added to each well. The RT mastermix contained 0.25 μl 200 U/μl SUPERCRIPT II (SuperScript II) (THERMOFISHER), 0.25 μl 40 U/μl RnaseOUT (THERMOFISHER), and 2.5 μl 2×RT mastermix. The 2×RT mastermix contained 1 μl 5×SuperScript II buffer (THERMOFISHER), 0.25 μl 100 mM DTT (THERMOFISHER), 1 μl 5 M betaine (SIGMA-ALDRICH), 0.03 μl 1 M $MgCl_2$ (SIGMA-ALDRICH), 0.125 μl 100 μM well-specific template switching oligonucleotide TSO_BCx_UMI5_TATA, and 0.095 μl PCR-grade $H_2O$ (QIAGEN). Reverse transcription was performed in a thermal cycler (lid temperature 70° C.) by 90 min at 42° C., followed by 10 cycles of 2 min at 50° C. and 2 min at 42° C., then 15 min at 70° C. Plates with single-cell cDNA were stored at −20° C. until further processing.

For cDNA amplification, 7.5 μl LD-PCR mastermix were added to each well. The LD-PCR mastermix contained 6.25 μl 2× KAPA HIFI HOTSTART READYMIX (KAPA HiFi HotStart ReadyMix™) (an amplification mix available from Roche Diagnostics), 0.125 μl 20 uM PCR_Satija forward primer, 0.125 μl 20 μM SmarterR reverse primer, and 1 μl PCR-grade $H_2O$ (QIAGEN). The amplification was performed in a thermal cycler (lid temperature 98° C.) by 3 min at 98° C., followed by 22 cycles of 15 sec at 98° C., 20 sec at 67° C., 6 min at 72° C., then a final elongation for 5 min at 72° C. Plates with amplified single-cell cDNA were stored at −20° C. until further processing.

For library preparation, 5 μl amplified cDNA from each well of a 96-well plate were pooled and completed to 500 μl with PCR-grade $H_2O$ (Qiagen). Two rounds of 0.6× solid-phase reversible immobilization beads (AMPUREXP (AmpureXP™), available from BECKMAN, or CLEANNGS (CleanNGS™), available from Proteigene) cleaning were used to purify 100 μl pooled cDNA with final elution in 15 μl PCR-grade $H_2O$ (Qiagen). After quantification with Qubit dsDNA HS assay (THERMOFISHER), 800 μg purified cDNA pool were processed with the Nextera XT DNA sample Preparation kit (ILLUMINA), according to the manufacturer's instructions with modifications to enrich 5'-ends of tagmented cDNA during library PCR. After tagmentation and neutralization, 25 μl tagmented cDNA was amplified with 15 μl Nextera PCR Mastermix, 5 μl Nextera i5 primer (S5xx, Illumina), and 5 μl of a custom 17 primer mix (0.5 μM i7_BCx+10 UM i7_primer). The amplification was performed in a thermal cycler (lid temperature 72° C.) by 3 min at 72° C., 30 sec at 95° C., followed by 12 cycles of 10 sec at 95° C., 30 sec at 55° C., 30 sec at 72° C., then a final elongation for 5 min at 72° C. The resulting library was purified with 0.8× solid-phase reversible immobilization beads (AmpureXP, Beckman, or CleanNGS, Proteigene).

Libraries generated from multiple 96-well plates of single cells and carrying distinct i7 barcodes were pooled for sequencing on an Illumina NextSeq550 platform, with High Output 75 cycles flow cells, targeting $5\times10^5$ reads per cell in paired-end single-index mode with the following primers and cycles: Read1 (Read1_SP, 67 cycles), Read i7 (17_SP, 8 cycles), Read2 (Read2_SP, 16 cycles).

Single-Cell RNAseq Data Processing

We used a custom bioinformatics pipeline to process fastq files and generate single-cell gene expression matrices and BCR or TCR sequence files. Detailed instructions for running the FB5P-seq bioinformatics pipeline can be found at https://github.com/MilpiedLab/. Briefly, the pipeline to obtain gene expression matrices was adapted from the Drop-seq pipeline, relied on extracting the cell barcode and UMI from Read2 and aligning Read1 on the reference genome using STAR and HTSeqCount. For BCR or TCR sequence reconstruction, we used Trinity for de novo transcriptome assembly for each cell based on Read1 sequences, then filtered the resulting isoforms for productive BCR or TCR sequences using MigMap, Blastn and Kallisto. Briefly, MigMap was used to assess whether reconstructed contigs corresponded to a productive V (D) J rearrangement and to identify germline V, D and J genes and CDR3 sequence for each contig. For each cell, reconstructed contigs corresponding to the same V (D) J rearrangement were merged, keeping the largest sequence for further analysis. We used Blastn to align the reconstructed BCR or TCR contigs against reference sequences of constant region genes, and discarded contigs with no constant region identified in-frame with the V (D) J rearrangement. Finally, we used the pseudoaligner Kallisto to map each cell's FB5Pseq Read1 sequences on its reconstructed contigs and quantify contig expression. In cases where several contigs corresponding to the same BCR or TCR chain had passed the above filters, we retained the contig with the highest expression level.

The per well accuracy (FIG. 3B) was computed as the Pearson correlation coefficient between $\log_{10}(UMI_{ERCC\text{-}xxxxx}+1)$ and $\log_{10}$ $(\#mol_{ERCC\text{-}xxxxx}+1)$, where UMIERCC-xxxxx is the UMI count for gene ERCC-xxxxx in the well, and #molERCC-xxxxx is the actual number of molecules for ERCC-xxxxx in the well (based on a 1:2,000,000 dilution in 2 μl lysis mix per well). For each well, only ERCC-xxxxx which were detected ($UMI_{ERCC\text{-}xxxxx}$>0) were considered for calculating the accuracy.

To estimate sensitivity (FIG. 3C), the percentage of wells with at least one molecule detected ($UMI_{ERCC\text{-}xxxxx}$>0) was calculated over all the wells from 5 or 6 96-well plates corresponding to human B cells sorted from Tonsil 1 or Tonsil 2, respectively. The value for each ERCC-xxxxx gene was plotted against log 10 ($\#mol_{ERCC\text{-}xxxxx}$) and a standard curve was interpolated with asymmetric sigmoidal 5PL model in GraphPad Prism 8.1.2 to compute the EC50 for each dataset.

The normalized coverage over genes (data not shown) was computed with RSeQC geneBody_coverage on bam files from 11 scRNAseq 96-well plates corresponding to human B cells sorted from Tonsil 1 and Tonsil 2.

Single-Cell Gene Expression Analysis

Quality control was performed on each dataset (Tonsil 1, Tonsil 2, T cells) independently to remove poor quality cells. Cells with less than 250 genes detected were removed. We further excluded cells with values below 3 median absolute deviations (MADs) from the median for UMI counts, for the number of genes detected, or for ERCC accuracy, and cells with values above 3 MADs from the median for ERCC transcript percentage.

For each cell, gene expression UMI count values were log normalized with Seurat v3 NormalizeData with a scale factor of 10,000. Data from B cells of Tonsil 1 and Tonsil 2 were analyzed together. Data from C.alb-specific T cells were analyzed separately. Four thousand variable genes, excluding identified with Seurat FindVariableFeatures. After scaling with Seurat Scale Data, principal component analysis was performed on variable genes with Seurat RunPCA, and embedded in two-dimensional tSNE plots with Seurat RunTSNE on 40 principal components. Cell cycle phases were attributed with Seurat CellCycleScoring. Plots showing tSNE embeddings colored by index sorting protein expression or other metadata (including BCR or TCR sequence related informations) were generated with ggplot2 ggplot. Plots showing tSNE embeddings colored by gene expression were generated by Seurat FeaturePlot. Gene expression heatmaps were plotted with a custom function (available upon request).

Results

FB5Pseq Experimental Workflow

We based the design of the FB5Pseq experimental workflow on existing full-length[3] and 5'-end[4,5] scRNAseq protocols. The main originalities in FB5Pseq were to perform cell-specific barcoding and incorporate 5 bp UMI during reverse transcription, and sequence the 5'-ends of amplified cDNAs from their 3'-end, and not from the transcription start site (FIG. 1A-B). In FB5Pseq, single cells of interest are sorted in 96-well plates by FACS, routinely using a 10-color staining strategy to identify and enrich for specific subsets of B or T cells while recording all parameters through index sorting. Single-cells are collected in lysis buffer containing External RNA Controls Consortium (ERCC) spike-in mRNA (0.025 μg per well) and sorted plates are immediately frozen on dry ice and stored at −80° C. until further processing. The amount of ERCC spike-in mRNA added to each well was optimized to yield around 5% of sequencing reads covering ERCC genes when studying lymphocytes which generally contain little mRNA. mRNA reverse transcription (RT), cDNA 5'-end barcoding and PCR amplification are performed with a template switching (TS) approach. Notably, our TSO design included a PCR handle (different from the one introduced at the 3'-end upon RT priming), an 8 bp well-specific barcode followed by a 5 bp UMI, a TATA spacer6, and three riboguanines. We empirically selected the 96 well-specific barcode sequences to avoid TSO concatemers in FB5Pseq libraries. After amplification, barcoded full-length cDNA from each well are pooled for purification and one-tube library preparation. For each plate, an Illumina sequencing library targeting the 5'-end of barcoded cDNA is prepared by a modified transposase-based method incorporating a plate-associated i7 barcode. The FB5Pseq library preparation protocol is cost-effective (260 € for library preparation of a 96-well plate), easily scalable and may be implemented on a pipetting robot.

FB5Pseq libraries are sequenced in paired-end single-index mode with Read1 covering the gene insert from its 3'-end, Read i7 assigning the plate barcode, and Read2 covering the well barcode and UMI. Because FB5Pseq libraries have a broad size distribution, with a gene insert of 100-850 bp, Read 1 sequences cover the 5'-end of transcripts approximately from 30 to 850 bases downstream of the transcription start site. Consequently, sequencing reads cover the whole variable and a significant portion of the constant region of the IGH and IGK/L expressed mRNAs (FIG. 1), enabling in silico assembly and reconstitution of BCR repertoire from scRNAseq data. Because TCRa and TCRβ genes share a similar structure, FB5Pseq is equally suitable for reconstructing TCR repertoire from scRNAseq data when T cells are analyzed.

FB5Pseq Bioinformatics Workflow

The FB5Pseq data is processed to generate both a single-cell gene count matrix and single-cell BCR or TCR repertoire sequences when analyzing B cells or T cells, respectively. After extracting the well-specific barcode and UMI from Read2 sequences and filtering out low quality or unassigned reads, we use two separate pipelines for gene expression and repertoire analysis (FIG. 2). The transcriptome analysis pipeline was derived from the Drop-seq pipeline[7]. Briefly, it consists of mapping all Read1 sequences to the reference genome, then quantifying, for each gene in each cell, the number of unique molecules through UMI sequences. After merging the data from all 96-well plates in the experiment, we filter the resulting gene-by-cell count matrices to exclude low quality cells, and normalize by total UMI content per cell.

For the extraction of BCR or TCR repertoire sequences from FB5Pseq data, we have developed our own pipeline based on de novo single-cell transcriptome assembly and mapping of reconstituted long transcripts (contigs or isoforms) on public databases of variable immunoglobulin or TCR genes. We identify and select contigs corresponding to productive V (D) J rearrangements in-frame with an identified constant region gene. In cases where multiple isoforms are identified for a given chain (e.g. IGH) in a single cell, we assign the most highly expressed isoform and discard the other one(s). In early validation experiments, our pipeline was equally efficient and accurate as RT-PCR followed by Sanger sequencing for IGH variable region analysis (data not shown), with the major advantage of retrieving complete variable regions and large portions of constant regions of both IGH and IGK/L, or TCRA and TCRB, from the same scRNAseq run.

FB5Pseq Quality Metrics on Human Tonsil B Cell Subsets

Figures 3A, 3B, 3C, 3D, 3E:
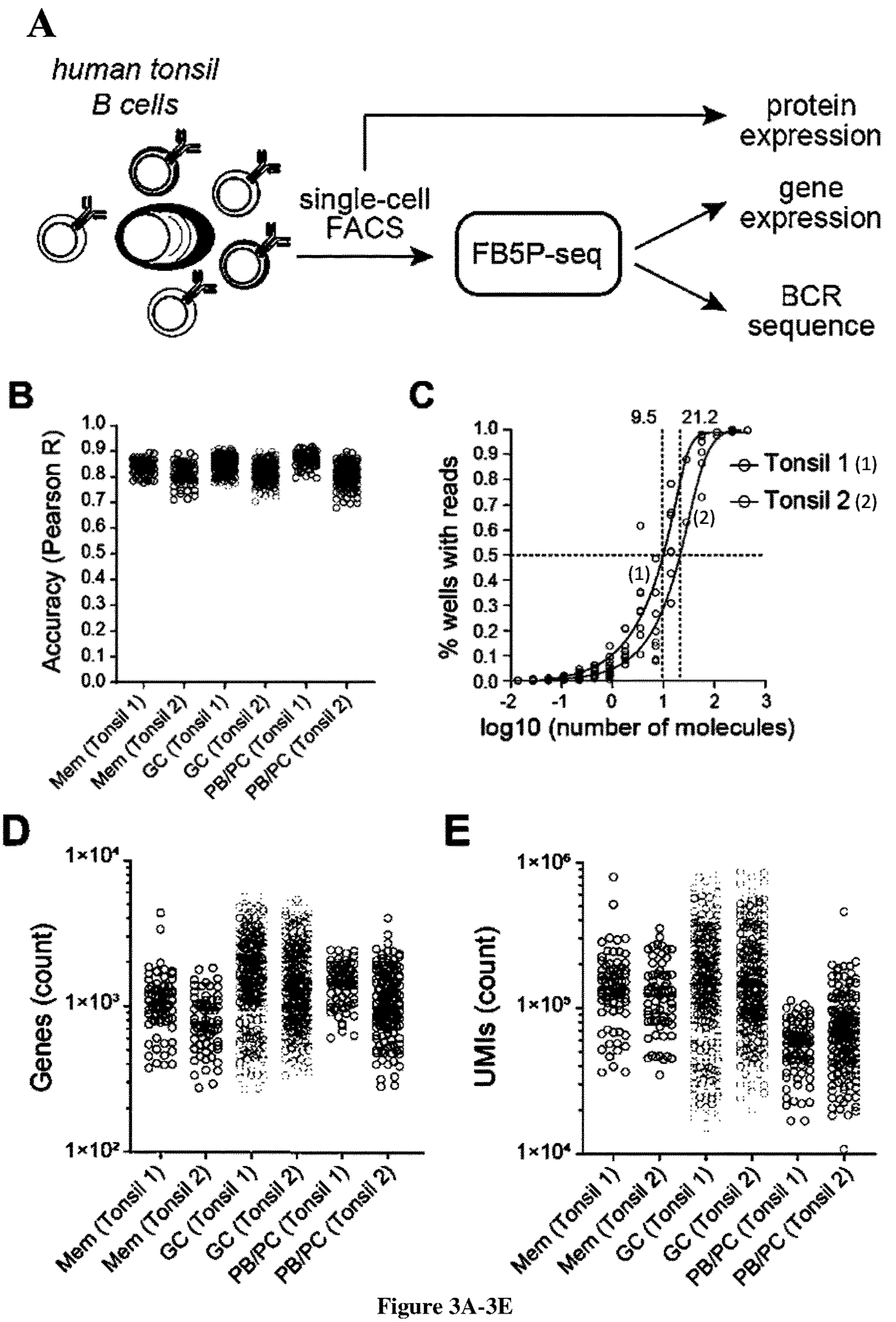

To illustrate the performance of our scRNAseq protocol, we obtained non-malignant tonsil cell suspensions from two adult human donors, referred to as Tonsil 1 and Tonsil 2. Based on surface marker staining, we excluded monocytes, T cells and naïve B cells, and sorted memory (Mem) B cells, germinal center (GC) B cells, and plasmablasts or plasma cells (PB/PCs) for FB5Pseq analysis (FIG. 3A). We processed Tonsil 1 and Tonsil 2 samples in two separate experiments, generating libraries from 5 and 6 plates respectively. Libraries were sequenced at an average depth of approximately 500,000 reads per cell (data not shown). After bioinformatics quality controls, we retained more than 90% of cells in the gene expression dataset (data not shown). We computed per cell accuracy (FIG. 3B) and per experiment sensitivity (FIG. 3C) based on ERCC spike-in detection levels and rates, respectively[1,2]. All cells showed high quantitative accuracy independently of their phenotype, with an overall mean correlation coefficient of 0.83 (FIG. 3B). The molecular sensitivity ranged from 9.5 to 21.2 (FIG. 3C), which compares favorably with other current scRNAseq protocols[2]. We detected a mean of 987, 1712 and 1307 genes per cell in Mem B cells, GC B cells and PB/PCS, respectively (FIG. 3D). GC and Mem B cells displayed higher total molecule counts (mean UMI counts of 192,765 and 145,356, respectively) than PB/PCs (mean UMI count of 67,861) (FIG. 3E).

Figure 3F:
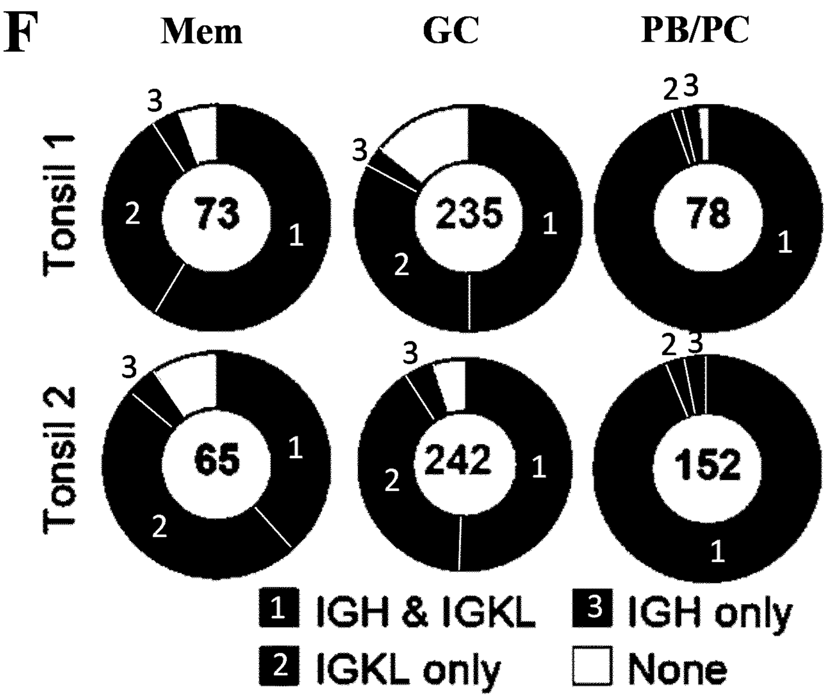

As expected from the method design, FB5Pseq Read1 sequence coverage was biased towards the 5'-end of gene bodies, with a broad distribution robustly covering from the 3rd to the 60th percentile of gene body length on average (data not shown). In Tonsil 1 and Tonsil 2 B cell subsets, the BCR reconstruction pipeline retrieved at least one productive BCR chain for the majority of the cells (FIG. 3F). Consistent with high expression of BCR gene transcripts for sustained antibody production, we obtained the paired IGH and IGK/L repertoire for the vast majority of PB/PCs. In Mem and GC B cells, we obtained paired IGH and IGK/L sequences on approximately 50% of the cells, and only the IGK/L sequence in most of the remaining cells. The superior recovery of IGK/L sequences was likely because the expression level of IGK/L was about 2-fold higher than IGH in our FB5Pseq data (data not shown).

Altogether, accuracy, sensitivity, gene coverage and BCR sequence recovery highlighted the high performance of the FB5Pseq method for integrative analysis of transcriptome and BCR repertoire in single B cells.

FB5Pseq Analysis of Human Tonsil B Cell Subsets

As a biological proof-of-concept, we further analyzed the Tonsil 1 and Tonsil 2 datasets. T-distributed stochastic neighbor embedding (t-SNE) analysis on the gene expression data discriminated three major cell clusters. Tonsil B cells clustered based on their sorting phenotype (Mem B cells, GC B cells or PB/PC) and did not cluster by sample origin (data not shown). Cell cycle status further separated the cycling (S and G2/M phase) from the non-cycling (G1) GC B cells (data not shown). The expression levels of surface protein markers recorded through index sorting were consistent with the gating strategy of Mem B cells ($CD20^{+}CD38^{lo}CD10^{-}CD27^{+}$), GC B cells ($CD20^{+}CD38^{+}CD10^{+}$) and PB/PCs ($CD38^{hi}CD27^{hi}$) (data not shown). The expression of the corresponding mRNAs mirrored the protein expression (data not shown), but revealed numerous cells where the mRNA was undetected despite intermediate or high levels of the protein. Further, we detected the expression of known marker genes for Mem B cells (CCR7, SELL, GPR183) GC B cells (AICDA, MKI67, CD81) or PB/PC (XBP1, PRDM1, IRF4) in the corresponding clusters (data not shown), and identified the top marker genes for each cell subset (data not shown). Those analyses were consistent with previous single-cell qPCR analyses[8] and bulk microarray analyses of human B cell subsets[9,10].

Figures 4A, 4B:
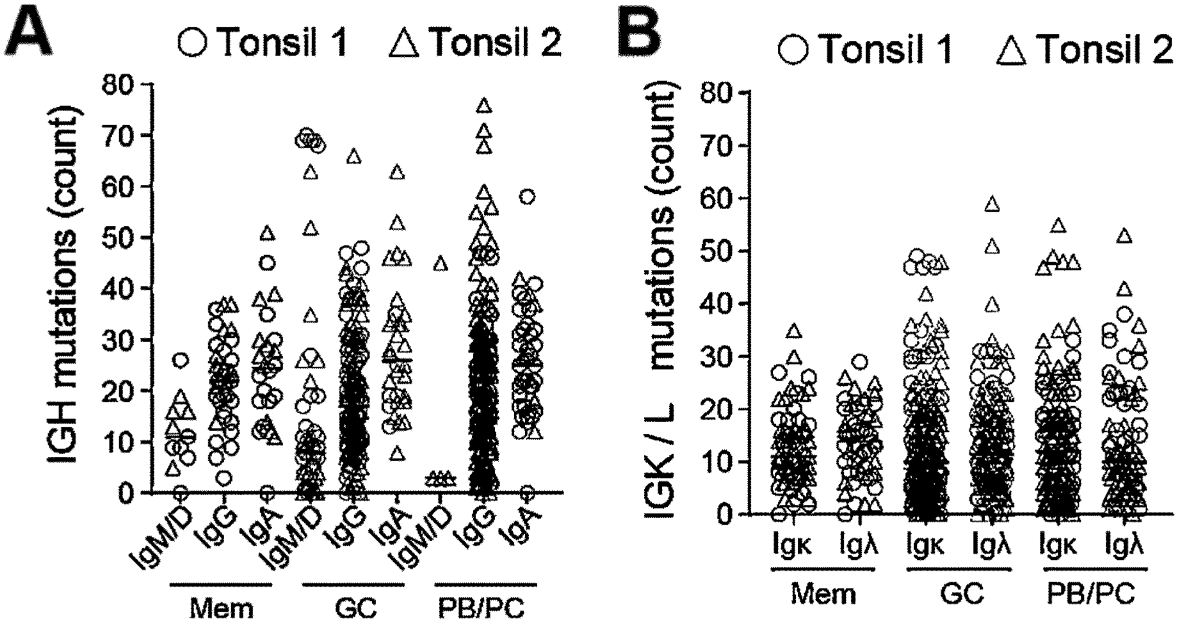

Integrating the single-cell BCR repertoire data to the t-SNE embedding, we revealed that the IGH and IGK/L repertoire of tonsil B cell subsets was polyclonal (data not shoown). Interestingly, while the somatic mutation load was equivalent in Igκ and Igλ light chains from Mem B cells, GC B cells and PB/PCs (FIG. 4B), the IGH mutation rate depended on isotype, with $IgA^{+}$ cells expressing the most mutated BCR (FIG. 4A) regardless of phenotype or sample origin. By contrast, $IgM/IgD^{+}$ cells exhibited the lowest somatic mutation loads (FIG. 4A).

Overall, those analyses confirmed that the FB5Pseq method is relevant for simultaneous protein, whole-transcriptome and BCR sequence analysis in human B cells.

FB5Pseq Analysis of Human Tonsil B Cell Subsets

Figures 5A, 5B, 5C, 5D, 5E:
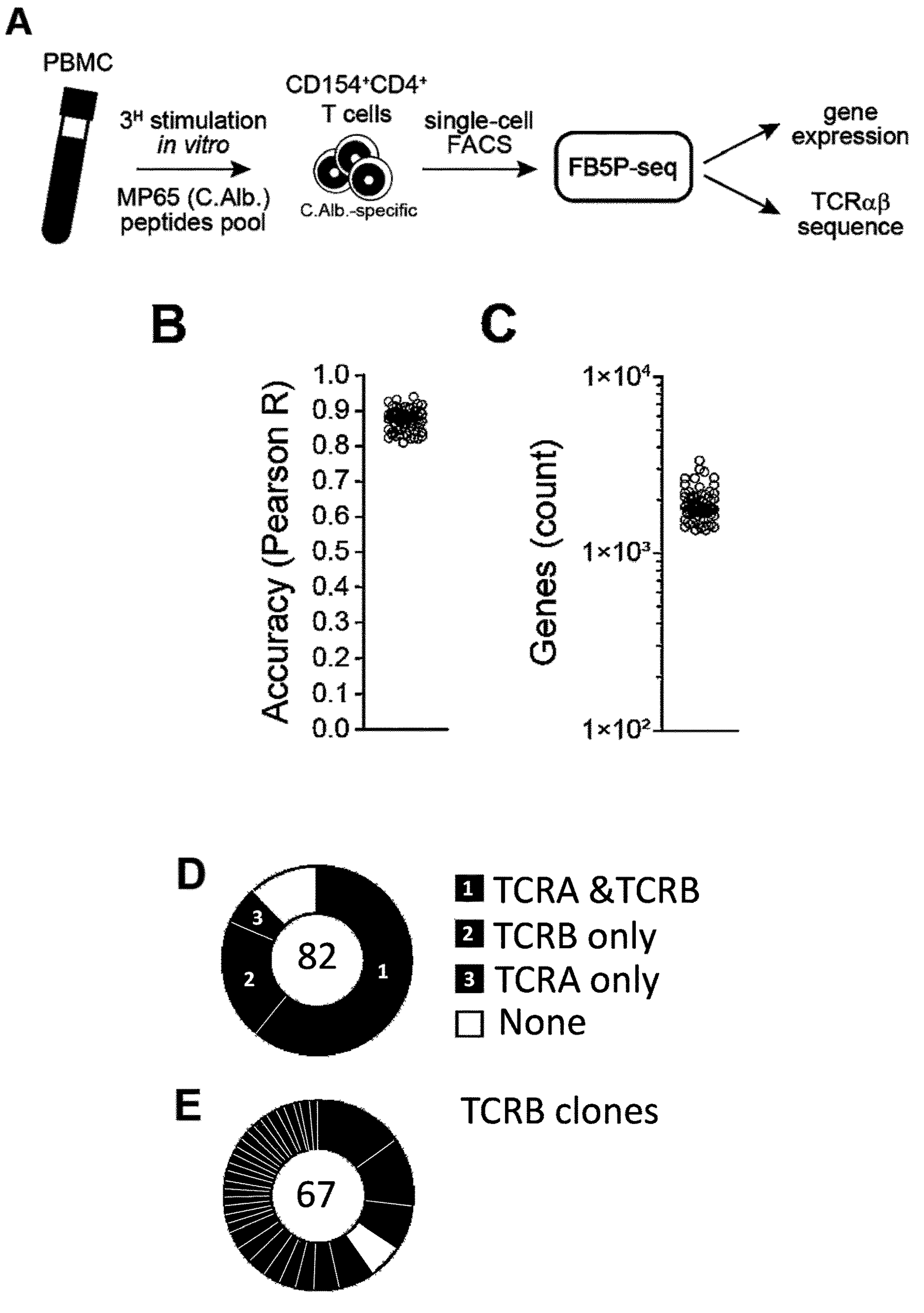

To test whether our protocol is also effective in T cells, we applied FB5Pseq to *Candida albicans*-specific human CD4 T cells sorted after a brief restimulation of fresh peripheral blood mononuclear cells with a pool of MP65 antigen-derived peptides (FIG. 5A and Methods). *Candida albicans* is a common commensal in humans, known to generate antigen-specific circulating memory CD4 T cells with a TH17 profile. Similar to the B cell dataset, the T cell dataset displayed high per cell accuracy (FIG. 5B) and an average of 1890 detected genes per cell (FIG. 5C). Gene expression analysis showed an efficient detection of T cell marker genes (CD3E), activation genes (CD40LG, EGR2, NR4A1, IL2), and TH17-specific genes (CCL20, CSF2, IL22, IL23A, IL17A) in those reactivated antigen-specific T cells (data not shown). We recovered at least one productive TCRa or TCRβ chain in 88% of cells, and paired TCRαβ repertoire in 61% of cells (FIG. 5D). Moreover, CDR3β sequence analysis revealed some expanded TCRβ clonotypes likely related to MP65 antigen-specificity (FIG. 5E). Principal Component Analysis (PCA) of the gene expression data and visualization of $V_{\beta}$-$J_{\beta}$ TCR rearrangements revealed no apparent segregation of antigen-specific T cells expressing different clonotypes (data not shown).

Taken together, these data indicate that our method is also relevant for integrative single-cell RNAseq analysis of human T cells.

Example 2

We adapted FB5P-seq to study the transcriptional response of human GC B cells to diverse combinations of stimuli by bulk RNA-seq. Briefly, we bulk-sorted GC B cells from human tonsils by FACS, and cultured them in vitro in the presence of any possible combination of five stimuli (IL4, IL10, IL21, CD40L, anti-BCR, 32 combinations in total) at a density of 500 cells per well. After 6 hours, cells were washed in PBS, lyzed in RLT buffer, and RNA was captured by SPRI bead precipitation. The captured RNA was then eluted in FB5P-seq lysis buffer, and each 500-cell RNA sample was processed with the adapted FB5P-seq protocol (with only 16 cycles of PCR for cDNA amplification). Libraries corresponding to four 96-well plates (3 human donors×32 conditions×3 replicates+control conditions) were prepared and sequenced on a 75 cycles HighOutput Illumina NextSeq550 run, generating RNA-seq results for over 300 samples in a single run.

The corresponding data were analyzed to identify the top 10 induced genes by single-stimulus activation and their expression in all combinations (data not shown).

REFERENCES

Throughout this application, various references describe the state of the art to which this invention pertains. The disclosures of these references are hereby incorporated by reference into the present disclosure.

1. Ziegenhain, C. et al. Comparative Analysis of Single-Cell RNA Sequencing Methods. *Molecular Cell* 65, 631-643.e4 (2017).
2. Svensson, V. et al. Power analysis of single-cell RNA-sequencing experiments. *Nat Meth* 14, 381-387 (2017).
3. Picelli, S. et al. Full-length RNA-seq from single cells using Smart-seq2. *Nat Protoc* 9, 171-181 (2014).
4. Satija, R., Farrell, J. A., Gennert, D., Schier, A. F. & Regev, A. Spatial reconstruction of single-cell gene expression data. *Nat. Biotechnol.* 33, 495-502 (2015).
5. Arguel, M.-J. et al. A cost effective 5' selective single cell transcriptome profiling approach with improved UMI design. *Nucleic Acids Res* 45, e48 (2017).
6. Tang, D. T. P. et al. Suppression of artifacts and barcode bias in high-throughput transcriptome analyses utilizing template switching. *Nucleic Acids Res* 41, e44 (2013).
7. Macosko, E. Z. et al. Highly parallel genome-wide expression profiling of individual cells using nanoliter droplets. *Cell* 161, 1202-1214 (2015).
8. Milpied, P. et al. Human germinal center transcriptional programs are de-synchronized in B cell lymphoma. *Nature Immunology* 19, 1013 (2018).
9. Victora, G. D. et al. Identification of human germinal center light and dark zone cells and their relationship to human B-cell lymphomas. *Blood* 120, 2240-2248 (2012).
10. Seifert, M. et al. Functional capacities of human IgM memory B cells in early inflammatory responses and secondary germinal center reactions. *Proc Natl Acad Sci USA* 112, E546-E555 (2015).

The invention claimed is:

1. A template switching oligonucleotide (TSO) comprising:

a 5'-terminal PCR handle sequence, a barcode sequence, a Unique Molecular Identifier (UMI) sequence, an insulator sequence, and a 3' terminal sequence consisting of 3 riboguanosine (rG), wherein the TSO consists of SEQ ID NO. 99 alone or in combination with one or more sequences selected from the group consisting of SEQ ID NO. 100 to SEQ ID NO. 194.

2. A method for preparing DNA that is complementary to an RNA molecule, the method comprising conducting a reverse transcription reaction with the RNA molecule in the presence of the template switching oligonucleotide (TSO) of claim 1.

3. An RNA sequencing method comprising the steps of:

a) providing a sample comprising RNA molecules, b) conducting reverse transcription (RT) of said RNA molecules by performing the method of claim 2, c) amplifying cDNAs obtained at step b), d) pooling and purifying the cDNAs, e) preparing a cDNA library from purified cDNAs obtained in step d), and f) sequencing said cDNA library.

4. A single-cell RNA sequencing method comprising the steps of:

a) isolating single cells,
b) lysing the single cells and extracting RNA molecules,
c) conducting reverse transcription (RT) of said RNA molecules by performing the method of claim 2,
d) amplifying cDNAs obtained at step c),
e) pooling and purifying the cDNAs,
f) preparing a cDNA library from purified cDNAs obtained in step e), and
g) sequencing said cDNA library.

5. The method of claim 3 wherein the step of conducting reverse transcription (RT) is performed using 96 different well-specific template switching oligonucleotides (TSO) to introduce a well-specific DNA barcode at the 5'-end of cDNAs, wherein said template switching oligonucleotides are sequences SEQ ID NOS: 99-194.

6. The method of claim 4 wherein the single cells are B cells and/or T cells.

7. The method of claim 4 wherein the step of lysing is performed with a lysis mixture comprising an RNase inhibitor, an amount of dNTP and an amount of a primer suitable for priming the reverse transcription of polyadenylated mRNAs while incorporating a universal PCR handle at the 3'-end of cDNA molecules, wherein the primer comprises the sequence TGCGGTATCTAAAGCGGT-GAGTTTTTTTTTTTTTTTTTTTTTTTTTTTTTT VN (SEQ ID NO:195), wherein V represents dG, dA, or dC and N represents dA, dT, dG, or dC.

8. The method of claim 3 wherein the step of amplifying is performed by PCR-based amplification and uses a pair of primers comprising a OK TO ENTER:/E.R.L./forward primer having the sequence AGACGTGTGCTCTTCC-GATCT (SEQ ID NO: 196) and a reverse primer having the sequence TGCGGTATCTAAAGCGGTGAG (SEQ ID NO:197).

9. The method of claim 3 wherein the step of preparing a cDNA library comprises subjecting the purified cDNAs to a tagmentation reaction with a plurality of adapters sequences as set forth in SEQ ID NOS: 214-229.

10. The method of claim 3 wherein the step of sequencing of the cDNA library is performed with the primers SEQ ID NOS: 230-232.

11. A method of performing an integrative analysis of a B and T cell transcriptome and paired T cell receptor (TCR)/B cell receptor (BCR) repertoire in phenotypically defined B and T cell subsets of a subject, comprising
a) obtaining from the subject B and T cells that are phenotypically defined,
b) lysing the B and T cells,
c) extracting RNA molecules from a lysate obtained in step b),
d) conducting reverse transcription (RT) of the RNA molecules to obtain cDNAs by performing the method of claim 5,
e) amplifying the cDNAs,
f) pooling and purifying the cDNAs to obtain purified cDNAs,
g) preparing a cDNA library from the purified cDNAs,
h) sequencing the cDNA library, and
i) performing the integrative analysis using sequence data obtained in the sequencing step.

12. A kit which comprises a plurality of TSO according to claim 1.

13. The kit of claim 12 which comprises the 96 TSO of SEQ ID NO: 99 to SEQ ID NO:194.

14. The kit of claim 12 which further comprises one or more of a panel of antibodies for cell sorting, primers, dNTPs, adapter sequences and/or a post synthesis labelling reagent, at least one buffer medium, and purification beads.

* * * * *